(12) United States Patent
Shou et al.

(10) Patent No.: US 8,377,883 B2
(45) Date of Patent: Feb. 19, 2013

(54) PEPTIDE FOR ANTI-ANGIOGENESIS AND USE THEREOF

(75) Inventors: Chengchao Shou, Beijing (CN); Yahui Su, Beijing (CN); Qin Feng, Beijing (CN)

(73) Assignee: Beijing Institute for Cancer Research, Beijing (CN)

( * ) Notice: Subject to any disclaimer, the term of this patent is extended or adjusted under 35 U.S.C. 154(b) by 664 days.

(21) Appl. No.: 12/443,684

(22) PCT Filed: Sep. 29, 2007

(86) PCT No.: PCT/CN2007/002850
§ 371 (c)(1),
(2), (4) Date: Dec. 2, 2009

(87) PCT Pub. No.: WO2008/040190
PCT Pub. Date: Apr. 10, 2008

(65) Prior Publication Data
US 2010/0111988 A1    May 6, 2010

(30) Foreign Application Priority Data
Sep. 30, 2006 (CN) .......................... 2006 1 0113568

(51) Int. Cl.
A61K 38/08 (2006.01)
A61K 38/10 (2006.01)
C07K 7/06 (2006.01)
C07K 7/08 (2006.01)

(52) U.S. Cl. ..................... 514/13.3; 514/19.3; 514/19.4; 514/19.6; 514/19.8; 514/21.5; 514/21.6; 514/21.8; 530/326; 530/327; 530/328; 530/329

(58) Field of Classification Search ........................ None
See application file for complete search history.

(56) References Cited

U.S. PATENT DOCUMENTS
6,569,845 B1 * 5/2003 Futamura et al. ............. 514/178

FOREIGN PATENT DOCUMENTS
| WO | 02088715 A2 | 11/2002 |
| WO | 03065997 A2 | 8/2003 |
| WO | 03070769 A2 | 8/2003 |
| WO | 2007022248 A2 | 2/2007 |

OTHER PUBLICATIONS

Marsh, Jr. et al. Mechanism of Action of Thrombin on Fibrinogen. Biochemistry. 1983, vol. 22, No. 18, pp. 4170-4174.*
International Search Report, mailed Jan. 3, 2008 for PCT/CN2007/002850, 9 pages.
International Preliminary Report on Patentability for Application PCT/CN2007/002850, mailed Mar. 31, 2009, 7 pages.
English Translation of Written Opinion of the International Searching Authority for Application PCT/CN2007/002850, mailed Jan. 3, 2008, 6 pages.

* cited by examiner

*Primary Examiner* — Jeffrey E Russel
(74) *Attorney, Agent, or Firm* — Schwabe, Williamson & Wyatt, P.C.

(57) ABSTRACT

The present invention relates to a peptide for anti-angiogenesis and use thereof, in particular, to a peptide useful for treating angiogenesis diseases; a polynucleotide coding the peptide; a vector and a cell comprising the polynucleotide; a pharmaceutical composition comprising the peptide, the fused peptide or the fused protein, the polynucleotide, the vector and/or the cell. The peptide, the fused peptide or the fused protein, the polynucleotide, the vector, the cell and/or the pharmaceutical composition can be used for treatment of associated diseases such as tumor by anti-angiogenesis.

15 Claims, 4 Drawing Sheets

PBS

FpAT

SEQUENCE LISTING

<160> NUMBER OF SEQ ID NOS: 17

<210> SEQ ID NO 1
<211> LENGTH: 15
<212> TYPE: PRT
<213> ORGANISM: Homo sapiens

<400> SEQUENCE: 1

Asp Ser Gly Glu Gly Asp Phe Leu Ala Glu Gly Gly Gly Val Arg
1               5                   10                  15

<210> SEQ ID NO 2
<211> LENGTH: 12
<212> TYPE: PRT
<213> ORGANISM: Homo sapiens

<400> SEQUENCE: 2

Glu Gly Asp Phe Leu Ala Glu Gly Gly Gly Val Arg
1               5                   10

<210> SEQ ID NO 3
<211> LENGTH: 9
<212> TYPE: PRT
<213> ORGANISM: Homo sapiens

<400> SEQUENCE: 3

Phe Leu Ala Glu Gly Gly Gly Val Arg
1               5

```
<210> SEQ ID NO 4
<211> LENGTH: 6
<212> TYPE: PRT
<213> ORGANISM: Homo sapiens

<400> SEQUENCE: 4

Glu Gly Gly Gly Val Arg
1               5

<210> SEQ ID NO 5
<211> LENGTH: 12
<212> TYPE: PRT
<213> ORGANISM: Homo sapiens

<400> SEQUENCE: 5

Asp Ser Gly Glu Gly Asp Phe Leu Ala Glu Gly Gly
1               5                   10

<210> SEQ ID NO 6
<211> LENGTH: 9
<212> TYPE: PRT
<213> ORGANISM: Homo sapiens

<400> SEQUENCE: 6

Asp Ser Gly Glu Gly Asp Phe Leu Ala
1               5

<210> SEQ ID NO 7
<211> LENGTH: 6
<212> TYPE: PRT
<213> ORGANISM: Homo sapiens

<400> SEQUENCE: 7

Asp Ser Gly Glu Gly Asp
1               5

<210> SEQ ID NO 8
<211> LENGTH: 6
<212> TYPE: PRT
<213> ORGANISM: Homo sapiens

<400> SEQUENCE: 8

Asp Phe Leu Ala Glu Gly
1               5

<210> SEQ ID NO 9
<211> LENGTH: 45
<212> TYPE: DNA
<213> ORGANISM: Homo sapiens
<220> FEATURE:
<221> NAME/KEY: misc_feature
<223> OTHER INFORMATION: n is a, c, g or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
```

```
<222> LOCATION: (27)..(27)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t

<400> SEQUENCE: 9
gayagnggng arggngaytt yctngcngar ggnggnggng tncgr          45

<210> SEQ ID NO 10
<211> LENGTH: 45
<212> TYPE: DNA
<213> ORGANISM: Homo sapiens

<400> SEQUENCE: 10
gatagtggtg aaggtgactt tctagctgaa ggaggaggcg tgcgt          45

<210> SEQ ID NO 11
<211> LENGTH: 3
<212> TYPE: PRT
<213> ORGANISM: Homo sapiens

<400> SEQUENCE: 11

Ala Glu Gly
1

<210> SEQ ID NO 12
<211> LENGTH: 4
<212> TYPE: PRT
<213> ORGANISM: Homo sapiens

<400> SEQUENCE: 12

Ala Glu Gly Gly
1

<210> SEQ ID NO 13
<211> LENGTH: 6
<212> TYPE: PRT
<213> ORGANISM: Homo sapiens

<400> SEQUENCE: 13

Leu Ala Glu Gly Gly Gly
1               5

<210> SEQ ID NO 14
<211> LENGTH: 5
<212> TYPE: PRT
```

```
<213> ORGANISM: Homo sapiens

<400> SEQUENCE: 14

Ala Glu Gly Gly Gly
1               5

<210> SEQ ID NO 15
<211> LENGTH: 5
<212> TYPE: PRT
<213> ORGANISM: Homo sapiens

<400> SEQUENCE: 15

Leu Ala Glu Gly Gly
1               5

<210> SEQ ID NO 16
<211> LENGTH: 6
<212> TYPE: PRT
<213> ORGANISM: Homo sapiens

<400> SEQUENCE: 16

Phe Leu Ala Glu Gly Gly
1               5

<210> SEQ ID NO 17
<211> LENGTH: 100
<212> TYPE: PRT
<213> ORGANISM: Homo sapiens

<400> SEQUENCE: 17

Arg Arg Gly Ala Glu Glu Ser Gly Pro Pro His Ser Pro Ser Arg Arg
1               5                   10                  15

Gly Ser Ala Ser Arg Ala Gly Pro Gly Arg Ala Ser Glu Thr Met Asn
                20                  25                  30

Phe Leu Leu Ser Trp Val His Trp Ser Leu Ala Leu Leu Leu Tyr Leu
            35                  40                  45

His His Ala Lys Trp Ser Gln Ala Ala Pro Met Ala Glu Gly Gly Gly
        50                  55                  60

Gln Asn His His Glu Val Val Lys Phe Met Asp Val Tyr Gln Arg Ser
65                  70                  75                  80

Tyr Cys His Pro Ile Glu Thr Leu Val Asp Ile Phe Gln Glu Tyr Pro
                85                  90                  95

Asp Glu Ile Glu
            100
```

PEPTIDE FOR ANTI-ANGIOGENESIS AND USE THEREOF

FIELD OF THE INVENTION

The present invention relates to a peptide and use thereof, particularly, to a peptide applicable to treatment of angiogenesis diseases, also to a polynucleotide coding the peptide, a vector and a cell comprising the polynucleotide, and a method and a pharmaceutical composition for treating angiogenesis diseases using the peptide, the polynucleotide, the vector or the cell.

SEQUENCE LISTING

The present application includes a Sequence Listing in electronic format as a text file titled "NCN090040US_Substitute_Seq_Listing2.txt" which was created on Oct. 2, 2012 and has a size of 4,078 bytes. The contents of txt file "NCN090040US_Substitute_Seq_Listing2.txt" are incorporated by reference herein.

BACKGROUND OF THE INVENTION

Tumor is one of the tough diseases threatening human health, and presently there are numerous methods for treating tumor. Anti-angiogenesis therapy developed on basis of the relationship between angiogenesis, and tumor growth and metastasis is a promising process, representing a new hope for tumor treatment. As early as 1970s, Folkman proposed that angiogenesis is the biological basis and an important scenario of malignant transformation, growth and metastasis of tumor and that angiogenesis inhibitors could become a new and valuable means to treat tumor. Malignant tumors without angiogenesis tend to be in a semi-dormant state, and are restricted to primary site, grow slowly and thus are unlikely to be too large. Tumors of a size over 2 $mm^3$~3 $mm^3$ require new blood vessels not only to maintain nutrition supply and excrete metabolites but also to provide favorable channels for their metastasis. With the proliferation of tumor cells, the enlargement of volume of tumor mass, and the change of the microcirculation of tumor mass, tumor cells and host cells are stimulated to produce pro-angiogenesis factors, the production of angiogenesis inhibitor is down-regulated, the balance therebetween in local tissue of tumor is broken, and angiogenesis is initiated, which represents the precondition of rapid proliferation of tumor. Once the new blood vessels formed, the tumor will grow logarithmically, and at the same time massive tumor cells transfer distally by means of the vessels, which have especially adverse effects on the condition and prognosis of patients. It was proved that the 5 years survival rate can be increased notably by using medicament to depress development of tumor and new blood vessels at the edges of tumor.

Based on many years of research on angiogenesis, O'Reilly and Folkman et. al. considered that there must exist pro-angiogenesis factors and angiogenesis inhibitors simultaneously in serums of tumor patients or of animals bearing tumor. These endogenous pro-angiogenesis factors and angiogenesis inhibitors act directly on the vascular endothelial cell in manners such as autocrine, paracrine or the like, influencing their proliferation, migration and formation of tubular structure, and the balance therebetween determines directly the initiation of tumor blood vessels and their developmental orientation, thus being the most important factor regulating tumor blood vessels. Among these, as a part of human endogenous proteins, endogenous inhibitors against tumor angiogenesis play a key role in controlling tumor growth and metastasis, thus represent a good perspective for cancer-resistance. Compared to other anti-tumor medicaments, the endogenous inhibitors against tumor angiogenesis possess many advantages as a medicament: (1) a treatment with the endogenous inhibitors against tumor angiogenesis has good specificity since the angiogenesis has already been initiated when the treatment is performed; (2) have a broad applications because the growth and the metastasis of all kinds of solid tumors depend on the angiogenesis; (3) the medicament can exert directly its effects since vascular endothelial cells expose to blood stream, which allows small dosage and high curative efficacy; (4) gene expressions are relatively stable in the endothelial cells, and it is unlikely to cause a resistance; (5) there is neither resistance caused by repeated administration and nor severe toxic side effect by the cytotoxic medicament. For example, endogenous anti-angiogenesis substances (endostatin) have made a success on the market in China. Many endogenous anti-angiogenesis formulations such as angiostatin and the like have also been in their clinical trials at various stages. Thus it can be seen that they represent a good perspective as candidate for medicament for treating tumors.

However, a long-term administration of the aforementioned endogenous anti-angiogenesis proteins will cause a resistance reaction due to its large molecular weight, low activity, inconvenience of synthesis, and weak immunogenicity for a formulation obtained via purification. In recent years, there is a tremendous development of the researches on endogenous anti-tumor peptide medicaments and derivative peptide medicaments thereof. The endogenous anti-tumor peptide medicaments and derivative peptide medicaments thereof have remarkable advantages over conventional anti-tumor medicaments: as messenger molecules they specifically kill or inhibit tumor cells in different scenarios of the growth and development of tumor cells. Furthermore, the peptides are easy to be synthesized due to their small molecular weight and simple structure, and have established and specific function with high activity, low toxic side effect and no immunogenicity, and thus are safe to be used as a medicament. In recent years, therefore, increasing attentions are drawn to the researches and developments of anti-tumor medicaments with the endogenous peptides and derivative peptides medicaments thereof as subjects.

Thus it can be seen that the endogenous anti-tumor angiogenesis inhibitor peptides have a great potential to be used as a candidate medicament for treating tumor as well as preventing postoperative tumor recurrence and metastasis.

BRIEF SUMMARY OF THE INVENTION

One object of the present invention is to provide a peptide or a pharmaceutically acceptable salt thereof.

Another object of the present invention is to provide the use of the peptide of the present invention or the pharmaceutically acceptable salt thereof in preparation of medicaments for treatment of the angiogenesis diseases.

Another object of the present invention is to provide a fused peptide or a fused protein comprising the peptide of the present invention.

Another object of the present invention is to provide a polynucleotide coding the peptide of the present invention.

Another object of the present invention is to provide a pharmaceutical composition comprising the peptide of the present invention or the pharmaceutically acceptable salt thereof, the fused peptide or the fused protein of the present invention, or the polynucleotide of the present invention; and a pharmaceutically acceptable carrier or excipient.

Another object of the present invention is to provide a vector comprising the polynucleotide of the present invention.

Another object of the present invention is to provide a cell comprising the polynucleotide or the vector of the present invention.

Another object of the present invention is to provide a method for treatment of angiogenesis diseases.

In one aspect, the present invention provide a peptide or a pharmaceutically acceptable salt thereof, the said peptide is a sequence having at least 40% of homology with the sequence (referred to as FpAT peptide herein) represented by the SEQ ID NO: 1 in Table 2 and having the same functions as SEQ ID NO: 1. Preferably the sequence of the peptide of the present invention has at least 45%, at least 50%, at least 55%, at least 60%, at least 65%, at least 70%, at least 75%, at least 80%, at least 85%, at least 90%, at least 91%, at least 92%, at least 95%, at least 96%, at least 97%, at least 98%, at least 99%, at least 99.5%, at least 99.8%, at least 99.9% of homology with the sequence represented by SEQ ID NO: 1.

In one embodiment of the present invention, there is provided a peptide as following (a) or (b) or a pharmaceutically acceptable salt thereof, wherein the peptide is (a) a peptide composed of the amino acid sequence represented by SEQ ID NO: 1;

(b) a peptide derived from (a) by subjecting the amino acid sequence in (a) to substitution, deletion and/or addition of one or more amino acids which has the same function as (a).

Since the sequence represented by SEQ ID NO: 1 of the present invention is a peptide of a sequence having only 15 amino acids, one skilled in the art can easily perform modifications conventional in the art to the amino acid sequence of SEQ ID NO: 1 without changing the functions thereof. The said modifications are, for example, performing manipulations such as conventional substitution, deletion or addition, and especially performing the substitution between the nonpolar amino acids or between the polar amino acids (particularly between the uncharged polar amino acids or between the polar amino acids with the same charge (positively charged or negatively charged)). For example, one skilled in the art can perform the substitution between the nonpolar amino acids or between the polar amino acids, such as replacement between Asp and Glu, using the classification of common amino acid sequences shown in Table 1.

TABLE 1

| Classification of amino acids | |
|---|---|
| nonpolar amino acids | Ala, Val, Leu, Ile, Met, Phe, Trp, Pro, eight in total |
| uncharged polar amino acids | Gly, Ser, Thr, Cys, Asn, Gln, Tyr, seven in total |
| positively charged | Arg, Lys, His |
| negatively charged | Asp, Glu |

Using analysis program (www.ebi.ac.uk/Tools/Sequence Analysis-ClustalW), the present inventor carried out a sequence alignment analysis of the homology of FpAT with VEGF (Vascular endothelial growth factor) according to the default parameters, and obtained a result that the six amino acids of Leu-Ala-Glu-Gly-Gly-Gly (SEQ ID NO: 13), at least five amino acids of Ala-Glu-Gly-Gly-Gly (SEQ ID NO: 14) are the important sequence of the peptide of the present invention (Example 3); this result is substantially consistent with a conclusion in the suppression of the tumor growth of mice of Kunming strain by FpAT and derivative peptides thereof in vivo, and in a experiment for the derivative peptides, the present inventor proved by intensive experiments that a peptide (FpAT-N5d-C4d of the present invention) composed of six successive amino acids of Asp-Phe-Leu-Ala-Glu-Gly (SEQ ID NO: 8) has a remarkable effect on treatment of the angiogenesis diseases. Taking the aforementioned results in account together, the present inventors proposed that Ala-Glu-Gly-Gly (SEQ ID NO: 12), particularly the successive amino acid sequence of Ala-Glu-Gly (SEQ ID NO: 11) of the present invention is a most crucial sequence of the peptide of the present invention. Based on these, one skilled in the art will appreciate that the substitution, deletion or addition to the sequences except the most crucial sequence of the present invention would not substantially change the functions of the peptide of the present invention.

The said homology can also be calculated according to a method known to one skilled in the art. For example, BEST-FIT program provided in UWGCG package can be used to calculate homology (Devereux et al. (1984) *Nucleic Acids Research* 12, pp. 387-395). BLAST algorithm can also be used to calculate homology or align sequence, for example, as described in *J Mol Biol* 215: pp. 403-410.

The compounds of the present invention can be used in a form of pharmaceutically acceptable salts. "Pharmaceutically acceptable salts" means suitable to contact with issues of human or animal without insufferable toxicities, stimulations, allergies, etc. The pharmaceutically acceptable salts are well known in the art. These salts may be prepared during the final isolation and purification of the peptides of the present invention or be prepared separately by reacting free base or acid with suitable organic or inorganic acid or base. Exemplary acid addition salts include, but not limited to, acetate, dicaproate, alginate, citrate, aspartate, benzoate, benzene sulfonate, bisulfate, butyrate, camphoric acid salt, camphorsulfonate, glycerophosphate, enanthate, caproate, fumarate, hydrochloride, hydrobromide, hydriodate, 2-hydroxyethyl sulfonate, lactate, maleate, methanesulfonate, nicotinic acid salt, 2-naphthalene sulfonate, oxalate, 3-phenyl propionate, propionate, succinate, tartrate, phosphate, glutamate, bicarbonate, p-toluenesulfonate, and hendecanoic acid salt. Preferred acids which can be used to form the pharmaceutically acceptable salts are hydrochloric acid, hydrobromic acid, sulphuric acid, phosphoric acid, oxalic acid, maleic acid, succinic acid, and citric acid. Cations in the pharmaceutically acceptable base addition salts include, but not limited to, alkali metal or alkaline earth metal ions such as lithium, sodium, potassium, calcium, magnesium, aluminium ion and the like, and nontoxic quarternary ammonium cations such as ammonium, tris(hydroxymethyl) aminomethane (Tris), tetramethyl ammonium, tetraethyl ammonium, methyl amine, dimethyl amine, trimethyl amine, triethyl amine, diethyl amine, ethyl amine, ethanolamine, diethanolamine, piperidine, piperazine, etc. Preferred pharmaceutically acceptable salts include phosphate, tris(hydroxymethyl) aminomethane, acetate.

The peptide of the present invention also can be derivative peptides of the sequence represented by SEQ ID NO: 1, preferably truncated sequences thereof, and preferably these derivative sequences comprising at least 4-successive amino acids sequence, and more preferable 5-, 6-, 7-, 8-, 9-, 10-, 11-, 12-, 13-, 14-successive amino acids of the sequence represented by SEQ ID NO: 1; the said successive amino acids are preferably Ala-Glu-Gly (SEQ ID NO: 11), more preferably Ala-Glu-Gly-Gly (SEQ ID NO: 14), and further preferably Leu-Ala-Glu-Gly-Gly (SEQ ID NO: 15) or Leu-Ala-Glu-Gly-Gly-Gly (SEQ ID NO: 13) or Phe-Leu-Ala-Glu-Gly-Gly (SEQ ID NO: 16). The said derivative peptide can be a sequence of at least 6, 7, 8, 9, 10, 11, 12, 13, 14 N-terminal amino acids of or a sequence of at least 6, 7, 8, 9, 10, 11, 12, 13, 14 C-terminal amino acids of the sequence represented by SEQ ID NO: 1, preferably the peptide is a sequence of at least 9 C-terminal amino acids of, and more preferably at least 12 C-terminal amino acids of the sequence represented by SEQ ID NO: 1 in Table 2; or the middle sequence corresponding to those lacking 5 N-terminal amino acids and 4 C-Terminal amino acids of the sequence represented by SEQ ID NO: 1 in Table 2. In particular, the peptide of the present invention can be those as shown in Table 2.

TABLE 2

Various small peptide sequences which have been used to perform experiments of animal tumor suppression

| | | |
|---|---|---|
| FpAT | Asp-Ser-Gly-Glu-Gly-Asp-Phe-Leu-Ala-Glu-Gly-Gly-Gly-Val-Arg | SEQ ID NO: 1 |
| FpAT-N3d | Glu-Gly-Asp-Phe-Leu-Ala-Glu-Gly-Gly-Gly-Val-Arg | SEQ ID NO: 2 |
| FpAT-N6d | Phe-Leu-Ala-Glu-Gly-Gly-Gly-Val-Arg | SEQ ID NO: 3 |
| FpAT-N9d | Glu-Gly-Gly-Gly-Val-Arg | SEQ ID NO: 4 |
| FpAT-C3d | Asp-Ser-Gly-Glu-Gly-Asp-Phe-Leu-Ala-Glu-Gly-Gly | SEQ ID NO: 5 |
| FpAT-C6d | Asp-Ser-Gly-Glu-Gly-Asp-Phe-Leu-Ala | SEQ ID NO: 6 |
| FpAT-C9d | Asp-Ser-Gly-Glu-Gly-Asp | SEQ ID NO: 7 |
| FpAT-N5d-C4d | Asp-Phe-Leu-Ala-Glu-Gly | SEQ ID NO: 8 |

In one embodiment of the present invention, the peptide of the present invention can be obtained by subjecting the sequence represented by SEQ ID NO: 1 to substitution, deletion and/or addition of one or more amino acids. The said substitution, deletion and/or addition are preferably the aforementioned substitution, deletion and/or addition occurring between polar amino acids or between the nonpolar amino acids, and particularly the substitution, deletion and/or addition between the polar amino acids or between the nonpolar amino acids performed to the sequences except the most crucial sequence (Ala-Glu-Gly; SEQ ID NO: 11), preferably except Ala-Glu-Gly-Gly (SEQ ID NO: 12), Leu-Ala-Glu-Gly-Gly (SEQ ID NO: 15), Leu-Ala-Glu-Gly-Gly-Gly (SEQ ID NO: 13) or Phe-Leu-Ala-Glu-Gly-Gly (SEQ ID NO: 16) of the peptide of the present invention.

The peptide of the present invention can be synthesized according to the conventional solid phase synthesis methods known to one skilled in the art. For example, the peptide of the present invention can be synthesized according to a method described by Steward and Young (Steward, J. M. and Young, J. D., Solid Phase Peptide Synthesis, 2$^{nd}$ Ed., Pierce Chemical Company, Rockford, Ill., (1984)), using Applied Biosystem synthesizer or Pioneer™ peptide synthesizer according to solid phase chemical techniques. With respect of solid phase peptide synthesis, many technical introductions can be found in Steward, J. M. and Young, J. D., Solid Phase Peptide Synthesis, W.H. Freeman Co. (San Francisco), 1963, and J. Meienhofer, Hormonal Proteins and Peptides, vol. 2, p. 46, Academic Press (New York), 1973. In general, these methods include successive addition of one or more amino acids or suitably protected amino acids to the growing chain of peptide. Generally, the amino group or the carboxyl group of the first amino acid is protected by suitable protective group, then the protected amino acid is linked to an inert solid phase support, followed by adding the corresponding next amino acid of the sequence with amino group or carboxyl group protected suitably, under the conditions allowing the formation of amide bond. Subsequently, the protective group is removed from the newly added amino acid residue, followed by adding the next amino acid which is protected suitably when necessary, and the operation is repeated similarly. When all amino acids are linked in the correct order, any remaining protective groups and solid phase support may be removed subsequently or simultaneously, thereby obtaining the finished polypeptide. More than one amino acid can be added at one time to the growing chain by modifying this general procedure simply.

A preferred method of preparing the shorter peptide of the present invention, such as FpAT peptide and derivative peptides thereof, is solid phase peptide synthesis, and in an embodiment of the present invention, the peptide of the present invention was prepared by using Pioneer™ peptide auto synthesizer, wherein the amino acids with α-amino group protected by groups sensitive to acid or base were used. These protective groups should be stable under the conditions of formation of peptide bonds, easy to remove without damaging the growing chain of peptide, and unlikely to cause racemation of any chiral centers. Suitable protective groups are 9-fluorene methoxy carbonyl (Fmoc), t-butoxy carbonyl (Boc), benzyloxy carbonyl (Cbz), 2-cyano t-butoxy carbonyl, etc. 9-fluorene methoxy carbonyl is particularly preferred to synthesis of the peptide of the present invention. Preparation of the longer peptide of the present invention is known in the art, which may be achieved by using a method of glutaraldehyde crosslinkage or by using a method of gene expression.

The research group to which the present inventor belongs found a low molecular weight differential protein which specifically presents in the serum of gastric carcinoma patients by using Surface-Enhanced Laser Desorption/Ionization and Time-of-Flight Mass Spectrometry technique, and upon tandem mass spectrometry analysis, the low molecular weight protein was found to be a peptide containing 15 amino acids, which corresponding to the carboxyl terminal 15 amino acids of fibrinopeptide A (FpA) (Example 1), therefore it was referred as FpAT (fibrinopeptide A truncated) by the present inventor. To further realize its biological activity, this peptide was synthesized chemically by the present inventor (Example 2), and it was found to exhibit a significant suppression on tumor growth upon intravenous injection to tumor-bearing mice (Examples 4 and 5). This effect was verified in repetitive experiments as well as in different models of mice tumor. Furthermore, when a histochemical analysis was performed on tumor mass of tumor-carrying mice, it was found that the microvessel density within tumor mass of tumor-bearing mice subjected to intravenous injection with peptides decreased notably; and when an immunohistochemical analysis was performed by using vascular endothelial cells labeled with antibody against Factor VIII, it was found that the microvessel density within tumor mass of the group administered with the peptides was dramatically lower than control group (P<0.05) (Example 6). In a model of suppression of blood vessel proliferation of chick chorioallantoic membrane, FpAT was found to suppress notably the formation of new blood vessel, and also induce disorder of blood vessel distribution, and atrophy of original blood vessel (Example 7). To further investigate the biological functions of FpAT peptide, based on repetitive verifications that this peptide possess anti-tumor growth activities with many repetitive experiments, the present inventor explored preliminarily the influence of FpAT peptide on growth of different cells in vitro, and found that FpAT peptide is capable of suppressing specifically the growth of vascular endothelial cell of mouse aorta and suppressing evidently proliferation, migration, and the ability to form a tubular structure of vascular endothelial cell of mouse aorta (Example 8). Influences of FpAT peptide on growths of different cells in vitro were explored preliminarily by using MTT experiments, and it was found that this peptide had not inhibitory effects on the growth of tumor cell in vitro (e.g. D2F2 cell) (Example 9), but had certain inhibitory effects on the growth of primary cultured human umbilical vein endothelial cell (HUVEC) and pig aorta endothelial cell (PAEC) (Example 10). Those results mentioned above proved definitely that FaAT peptide has notable suppressing effects on tumor growth via anti-angiogenesis. Moreover, the present inventor preliminary explored anti-angiogenesis mechanism of FpAT peptide and the suppressing activities of FpAT peptide on cell proliferation achieved via inducing apoptosis of vascular endothelial cells in experiments using flow cytometry method and DNA Ladder, and furthermore the present inventor explored preliminarily, using RT-PCR and Western blotting experiments, the mechanism of apoptosis of vascular endothelial cells by induction of FpAT peptide (Example 11). In a model of inducing vascular endothelial cells three-dimensional structure in vitro, it can be found that FpAT suppressed notably the ability to form tubular structure of vascular endothelial cells (Example 12), and it can be further found that FpAT peptide induced notably the disassembly of cytoskeleton microfilament in the stained microfilament of the cells treated with FpAT peptides and control cells (Example 13). It particularly should be noted that FpAT of the present invention and derivative peptides thereof can suppress, to various extents, the growth of mice liver cancer H22 cells in mice of Kunming strain in vivo, and retard the rate of tumor growth (Example 14).

Accordingly, another aspect of the present invention is to provide use of the peptide of the present invention or a pharmaceutically acceptable salt thereof in preparation of medicaments for treating angiogenesis diseases.

Specific examples of the said angiogenesis diseases include:

1) Diseases caused by dysfunctions or disorders in production or maturation of normal hemocytes:

abnormalities caused by highly division of stem cells; aplastic anemia; neutropenia; cells decreasing; anaemia; pancytopenia; agranulocytosis; thrombocytopenia; erythrocyte hypoplasia; Blackfan-Diamond syndrome caused by medicaments, radioactivity, or infection;

2) Hematological malignant tumors:

Including, but not limited to, the following hematological malignant tumors: acute lymphoblastic (lymphocytic) leukemia; chronic lymphocytic leukemia; acute marrow granulocyte leukemia; chronic marrow granulocyte leukemia; acute malignant myelosclerosis; multiple myeloma; polycythemia vera; waldenstrom macroglobulinemia; hodgkin's lymphoma; non-hodgkin's lymphoma;

3) Malignant tumors or solid tumors:

Including, but not limited to, the primary or metastatic solid tumors or carcinomas of the following organs: mammary gland, colon, rectum, lung, oropharynx, laryngopharynx, esophagus, stomach, pancreas, liver, gallbladder, bile duct, small intestine; urethra including kidney, urinary bladder and urinary epithelium; femal genital meatus, including uterine cervix, uterus, ovary, chorion carcinoma and pregnancy nutritive layer diseases; male genital meatus, including prostatic gland, seminal vesicle, and testis; endocrine glands, including thyroid gland, suprarenal gland, and pituitary gland; skin, including angiogenesis tumor, melanoma, sarcoma and Kaposi's sarcoma occurring bone or parenchyma; tumors of brain, nerve, eye and meninges, including astrocytoma, glioma, glioblastoma, retinoblastoma, neuroma, neuroblastoma, schwannoma, and neurilemmoma; liver cancer; osteosarcoma. And it is preferred to be liver cancer, lung cancer, esophageal carcinoma, gastric carcinoma, colorectal cancer, renal carcinoma, pancreatic carcinoma, osteosarcoma, or breast carcinoma.

4) Autoimmune diseases:

rheumatoid arthritis; type I diabetes; chronic hepatitis; multiple sclerosis; systemic lupus erythematosus;

5) Hereditary (congenital) disorders:

anaemia; familial aplastic anemia; Fanconi syndrome; Bloom's syndrome; pure red cell aplasia (PRCA); dyskeratosis congenital syndrome; Blackfan-Diamond syndrome; congenital erythrocyte regeneration defect syndrome I-IV; Chwachmann-Diamond syndrome; dihydrofolate reductase deficiency; formamino transferase deficiency; Lesch-Nyhan syndrome; congenital spherocytosis; congenital elliptocytosis; congenital stomatocytosis; congenital Rh null diseases; paroxysmal nocturnal hemoglobinuria; glucose-6-phosphate Dehydrogenase variants 1, 2, 3; pyruvate kinase deficiency; congenital low response to erythropoietin; Sickle-cell diseases and characteristics; Thalassemia α, β, γ; met-hemoglobinemia; Congenital immunodeficiency; severe combined immunodeficiency disease (SCID); bare lymphocyte syndrome; ionophore-responsive combined immunodeficiency; combined immunodeficiency with a capping abnormality; nucleoside phosphorylase deficiency; cranulocyte actin deficiency; agranulocytosis infantile; Gaucher's disease; adenosine deaminase deficiency; kostmann's syndrome; reticular cell hypoplasia; congenital leucocyte cacergasia syndrome;

6) Other diseases:

osteopetrosis; myelosclerosis; acquired hemolytic anemia; acquired immunodeficiency; primary or secondary immunodeficiency resulted from infectious diseases; bacterial infections (e.g. brucellosis, listeriosis, tuberculosis, leprosy); parasitic infection (e.g. malaria, leishmaniasis); fungal infection;

immune cacergasia caused by lymphocyte disproportionality resulted from cacergasia of aged bacterialphilic cells; Kostmann agranulocytosis; chronic granulomatous diseases; Chédiak-Higashi syndrome; Willams-Beuren syndrome; neutrophil actin deficiency; neutrophil cell membrane GP-180 deficiency; mucopolysaccharidosis; mucolipidosis; mixed immunodeficiency; Wiskott-Aldrich syndrome; α1-antitrypsin deficiency.

The peptide of the present invention and a pharmaceutically acceptable salt thereof further suppress tumor growth by suppressing tumor endothelial cells, thereby are capable of treating tumors as well as preventing postoperative tumor recurrence and metastasis. Thus preferably the peptide of the present invention or a pharmaceutically acceptable salt thereof can be used for tumor treatment and prevention of postoperative tumor recurrence and metastasis. The said tumors may be solid tumors or hematological malignant tumors (e.g. the aforementioned acute lymphoblastic (lymphocytic) leukemia; chronic lymphocytic leukemia; acute marrow granulocytes leukemia; chronic marrow granulocytes leukemia; acute malignant myelosclerosis; multiple myeloma; polycythemia vera; waldenstrom macroglobulinemia; hodgkin's lymphoma; non-hodgkin's lymphoma), but solid tumors are preferred. The said solid tumors may be, but not limited to, primary or metastatic solid tumors or carcinomas occurring in the following organs: mammary gland, colon, rectum, lungs, oropharynx, laryngopharynx, esophagus, stomach, pancreas, liver, gallbladder, bile duct, small intestine; urethra including kidney, urinary bladder and urinary epithelium; femal genital meatus, including uterine cervix, uterus, ovary, chorion carcinoma and pregnancy nutritive layer diseases; male genital meatus, including prostatic gland, seminal vesicle, and testis; endocrine glands, including thyroid gland, suprarenal gland, and pituitary gland; skin, including angiogenesis tumor, melanoma, sarcoma and Kaposi's sarcoma occurring in bone or parenchyma; tumors of brain, nerve, eye and meninges, including astrocytoma, glioma, glioblastoma, retinoblastoma, neuroma, neuroblastoma, schwannoma, and neurilemmoma; liver cancer; osteosarcoma. And it is preferred to be liver cancer, lung cancer, esophageal carcinoma, gastric carcinoma, colorectal cancer, renal carcinoma, pancreatic carcinoma, osteosarcoma, or breast carcinoma.

In an embodiment of the present invention, the said treatment of angiogenesis diseases is particularly anti-angiogenesis.

Another aspect of the present invention is to provide a fused peptide or a fused protein comprising the peptide of the present invention and the said peptide may be same or different sequences, optionally with a suitable linker between adjacent sequences. In other words, the peptide of the present invention may be linked one another optionally by a suitable linker, so as to form into a homo- or hetero-polymer. The peptide of the present invention may also be fused with other functional peptide(s) or protein(s), so as to form into different types of multifunctional fused peptide(s) or fused protein(s). For example, the peptide of the present invention can be combined to a fused peptide or a fused protein with the following polypeptides or proteins: 1) various cytokines such as one or more cytokines of IL-2, IL-12, IL-4, IL-24, GM-CSF-1, IFN-α, IFN-γ, MIP-1, PEDF, TSP-1, TIMP-1, TIMP-2, VEGI, and IL-8, so as to function as cytokines while suppressing tumor growth; 2) soluble receptors KDR or Flt-1, so as to play a double function of binding VEGF via the soluble receptors, while suppressing tumor growth; 3) specific antibodies or fragments thereof, such as specific antibodies against tumor blood vessel endothelium or fragments thereof, so as to impart a targeting distribution to the peptide of the present invention in vivo; 4) molecules such as B7, so as to activate lymphocytes locally around tumors while suppressing tumor growth; 5) any other peptides or proteins capable of being compatible, and functionally complementary or synergetic with the peptide of the present invention, such as endostatin, angiostatin, vasostatin, PEX, PF4, etc.

The fused peptides or fused proteins of the present invention can be produced by employing a recombinant method known in the art.

Another aspect of the present invention is to provide a polynucleotide coding the peptide of the present invention. It is known to one skilled in the art that a polynucleotide coding a peptide, such as, one represented by SEQ ID NO: 1, can be determined according to the codon corresponding to different amino acids; and of course, the said polynucleotide may have different forms due to the degeneracy of codon, and it is preferred to select relevant codon according to codon usage frequencies of different organisms. The polynucleotide sequence of the polypeptide of the present invention may be DNA or RNA, wherein DNA includes cDNA, genomic DNA and synthetic DNA, and DNA may be in the form of double-stranded or single-stranded, and single-stranded DNA may be a coding strand or a noncoding strand (antisense strand). The present invention provides a polynucleotide sequence coding the peptide represented by SEQ ID NO: 1 of the present invention, which is shown as SEQ ID NO: 9, and in this sequence, n at the nucleotide positions of No. 6, 9, 15, 24, 27, 33, 36, 39 and 42 can be any one of a, c, g, and t; y at the nucleotide positions of No. 3, 18 and 21 can be t or c; and r at the nucleotide positions of No. 12, 30 or 45 can be g or a. The present invention provides also preferred polynucleotide sequences coding the peptide represented by SEQ ID NO: 1 of the present invention, for example, SEQ ID NO: 10. Basing on this, one skilled in the art can easily determine the polynucleotide sequences coding other peptides.

In another aspect of the present invention, there is provided a vector comprising the polynucleotide of the present invention. Artificially constructed plasmids are usually used as vectors in genetic engineering. Artificially constructed plasmids can be integrated with a plurality of useful characteristics in one system, such as containing various single enzyme digesting sites, resistances to antibiotics, etc. Artificial plasmid vectors comprising the polynucleotide of the present invention include, for example, pBR322, pSC101, etc. Virus vector technology is a series of technique of packaging therapeutic genes and the expression elements thereof into certain virions to form recombinant virus, and performing production and purification in a large amount. The therapeutic genes can be transferred into cells efficaciously by these recombinant viruses to work as compensating, replacing, repairing the defective genetic functions, or killing abnormal cells such as tumor cells. The viruses useful as the vectors comprising the polynucleotide of the present invention mainly include retrovirus, adenovirus, adenovirus-associated viruses, herpes simplex virus, poxvirus, etc.

In another aspect of the present invention, there is provided a cell comprising the polynucleotide or the vector of the present invention. The cell include, but not limited to, prokaryotic host cells such as *Escherichia coli, Bacillus genus, Streptomyces* genus, etc.; eukaryotic host cells such as *Saccharomyces genus, Aspergillus* genus, insect cells such as *drosophila* S2 and *Spodoptera frugiperda* Sf9; animal cells such as CHO, COS (a cell line derived from the African green monkey kidney cells, Gluzman (Cell 23:175, 1981)), and other cell lines capable of expressing compatible vectors. Methods of transferring the polynucleotide of the present invention or the plasmid vector comprising the polynucleotide of the present invention into the aforementioned host cells are well known to one skilled in the art, which include, but not limited to, transformation mediated by calcium chloride, calcium phosphate transfection, transfection mediated by DEAE-glucan, electroporation, microinjection, particle bombardment method or gene gun method. It is also known to one skilled in the art a detailed method of transferring the gene comprising the peptide of the present invention into cells by means of the infectivity of virus vectors to host cells. The virus vectors are used widely due to having the characteristics of high transduction efficiency and high expression efficiency. The transformed host strains or cells are cultured in suitable culturing conditions and medium, and allowed to grow to a proper cell density. It is in the range of knowledge of one skilled in the art to select the corresponding culturing condition and medium according to different host strains or cells as well as the properties of target peptides to express. It is particularly important that the said cells may be derived from a patient oneself to treat, and after the cells are transfected with the peptides of the present invention conventionality, the transfected cells can be transported back to the patient, to treat angiogenesis diseases and reduce immunity-related symptom.

In another aspect of the present invention, there is provided a pharmaceutical composition comprising the peptide of the present invention or a pharmaceutically acceptable salt thereof, and/or the fused peptide or fused protein of the present invention, and/or the polynucleotide of the present invention, and/or the vector of the present invention, and/or the cell of the present invention; and a pharmaceutically acceptable carrier or excipient. The pharmaceutically acceptable carrier or excipient refers to a non-toxic filler, diluent agent, encapsulating material or other formulation auxiliary material in solid state, semisolid state or liquid state. The pharmaceutical composition may be produced, depending on the therapy purposes and the demand of administration approached, into various formulations such as solution, liposome encapsulates, microcapsule and other sustained released formulations. Examples of the pharmaceutically acceptable carrier or excipient include physiological saline, isotonic glucose solution, buffered saline, glycerol, ethanol and the combination of the aforementioned solutions. The adjuvant ingredients may be added to the composition as required, such as compounds which are synergetic with the peptide of the present invention; protein-protecting agents such as sero-albuminum humanum, low molecular weight peptides, amino acids and metal cations; and the like. The pharmaceutical composition of the present invention can still further include: 1) various cytokines such as one or more cytokines of IL-2, IL-12, IL-4, IL-24, GM-CSF-1, IFN-α, IFN-γ, MIP-1, PEDF, TSP-1, TIMP-1, TIMP-2, VEGI, and IL-8, so as to function as a cytokine while suppressing tumor growth; 2) soluble receptors KDR or Flt-1, so as to play a double function of binding VEGF by a soluble receptor while suppressing tumor growth; 3) specific antibodies or fragments thereof, such as specific antibodies against tumor blood vessel endothelium or fragments thereof, so as to impart a targeting distribution to the peptide of the present invention in vivo; 4) molecules such as B7, so as to activate lymphocytes locally around tumors while suppressing tumor growth; 5) with any other peptides or proteins capable of being compatible, and functionally complementary or synergetic with the peptide of the present invention, such as endostatin, angiostatin, vasostatin, PEX, PF4, etc.

In another aspect of the present invention, there is provided a method for treating angiogenesis diseases, which comprise administering to patients in need of this treatment a therapeutically effective amount of the peptide (FpAT, peptides homologous to, or derived from, FpAT) or a pharmaceutically acceptable salt thereof, the fused peptide or the fused protein, the pharmaceutical composition, the polynucleotide, the vector and/or the cell of the present invention. The therapy method of the present invention is particularly suitable to treat tumors and postoperative tumor recurrence and metastasis. The said tumors may be solid tumors or hematological malignant tumors (e.g. acute lymphoblastic (lymphocytic) leukemia; chronic lymphocytic leukemia; acute marrow granulocytes leukemia; chronic marrow granulocytes leukemia; acute malignant myelosclerosis; multiple myeloma; polycythemia vera; waldenstrom macroglobulinemia; hodgkin's lymphoma; non-hodgkin's lymphoma mentioned above), but solid tumors are preferred. The peptide of the present invention may be used to treat the primary or metastatic solid tumors or carcinomas of the following organs: mammary gland, colon, rectum, lung, oropharynx, laryngopharynx, esophagus, stomach, pancreas, liver, gallbladder, bile duct, small intestine; urethra including kidney, urinary bladder and urinary epithelium; femal genital meatus, including uterine cervix, uterus, ovary, chorion carcinoma and pregnancy nutritive layer diseases; male genital meatus, including prostatic gland, seminal vesicle, and testis; endocrine glands, including thyroid gland, suprarenal gland, and pituitary gland; skin, including angiogenesis tumor, melanoma, sarcoma and Kaposi's sarcoma occurring in bone or parenchyma; tumors of brain, nerve, eye and meninges, including astrocytoma, glioma, glioblastoma, retinoblastoma, neuroma, neuroblastoma, schwannoma, and neurilemmoma; liver cancer; osteosarcoma. And it is preferred to be liver cancer, lung cancer, esophageal carcinoma, gastric carcinoma, colorectal cancer, renal carcinoma, pancreatic carcinoma, osteosarcoma, or breast carcinoma.

The peptide or a pharmaceutically acceptable salt thereof, the fused peptide or the fused protein, the pharmaceutical composition, the polynucleotide, the vector and/or the cell of the present invention are suitable to intraocular, parenteral, sublingual, intracisternal, intravaginal, intraperitoneal, intrarectal, intrabuccal, intratumor or epidermal administration. The parenteral administration includes intravenous, intramuscular, intraperitoneal, intrasternal, subcutaneous, intraarthral injection and infusion. The epidermal administration includes administrations on skin, mucous membrane, as well as the surface of lung and eye. In a composition suitable to be inhaled, the peptide of the present invention may be pressurized or included in pressurized gas such as nitrogen gas or liquefied gas propellant. Preferably, the peptide of the present invention is not soluble in liquefied propellant medium. The compositions to be administered intrarectally or intravaginally are preferably a suppository, which may be prepared by mixing the peptide of the present invention with suitable nonirritative excipients or carriers such as cocoa butter, polyethylene glycol, or suppository wax; and the said excipients or carriers are in solid state at room temperature and liquid state at body temperature, and thus melt in rectum or vaginal cavity and release the active compound(s). In one preferred embodiment of the present invention, the administration is performed employing angulus oculi medialis vein injection.

When a therapy is carried out in the aforementioned manners or other manners, the peptide of the present invention in a therapeutically effective amount can be the peptide of the present invention per se, a pharmaceutically acceptable salt form, with or without pharmaceutically acceptable excipients or carriers. A therapeutically effective amount of the peptide of the present invention or a pharmaceutically acceptable salt thereof, the fused peptide or fused protein of the present invention, the polynucleotide of the present invention, the vector or the cell of the present invention, or the pharmaceutical composition of the present invention means an amount of the said substances which is effective for treating angiogenesis diseases. The specific therapeutically effective amount for any specific patients depends on many factors, which include the diseases to be treated and severity thereof; the activities of specific compounds used; the specific composition used; age, body weight, gender, diet and general healthy conditions of a patient; administrating time; administrating means; excretion rate of the specific compounds; duration of the therapy; other medicaments administered in combination or simultaneously. The peptide of the present invention or a pharmaceutically acceptable salt thereof, the fused peptide or fused protein of the present invention, the polynucleotide of the present invention, the vector or the cell of the present invention, or the pharmaceutical composition of the present invention can be administered once or more than one time per day, so that a single dosage form can contain the whole or the partial amount of a daily dosage; and also can be administered once during a period of time (e.g. 2 days, 3 days, 5 days or the like). A therapeutically effective amount of the peptide of the present invention is preferable 0.001 μg/kd/d to 500 mg/kg/d.

A plenty of experiments have confirmed that the peptide of the present invention can treat angiogenesis diseases efficaciously (see Examples 4 to 14 for details), thereby providing a novel and effective approach for treating angiogenesis diseases, particularly for anti-angiogenesis. This has a great sense to tumor treatment and prevention of postoperative tumor recurrence and metastasis. The peptide of the present invention has not only many advantages of endogenous angiogenesis inhibitor but also many advantages such as small molecule, high activities, being easy to synthesize, and the like.

BRIEF DESCRIPTION OF THE DRAWING

FIG. 1A and FIG. 1B show the determination of FpAT sequence, in which FIG. 1A shows the distribution of FpAT (1468 Da) in serum of gastric carcinoma and normal control; and FIG. 1B shows sequencing results of the 1468 Da peptide by SELDI-TOF-MS-MS.

FIG. 2A and FIG. 2B show the suppression of tumor growth in mice of Kunming strain by FpAT in vivo, in which FIG. 2A shows a liver cancer H22 cells tumor-bearing mouse model of mice of Kunming strain; and FIG. 2B shows a osteosarcoma S180 cells tumor-bearing mouse model of mice of Kunming strain.

FIG. 3A, FIG. 3B and FIG. 3C show the suppression of tumor growth in nude mice by FpAT in vivo, in which FIG. 3A shows a human gastric carcinoma 823 cells tumor-bearing mouse model of nude mice; FIG. 3B shows a tumor-carrying nude mice model of human lung cancer PG cells; and FIG. 3C shows a human colon cancer HT-29 cells tumor-bearing mouse model of nude mice.

FIG. 9A, FIG. 9B and FIG. 9C show that FpAT's specific suppression on proliferation activities of vascular endothelial cells is achieved by inducing apoptosis of the vascular endothelial cells, in which FIG. 9A shows that FpAT has no remarkable effects on cell cycle of HUVECs (human umbilical vein endothelial cells), but the presence of an obvious apoptosis peak was found with flow cytometry analysis, which proved that FpAT can induce apoptosis of HUVECs; FIG. 9B shows the presence of plenty of DNA Ladder in total DNA extracted from FpAT treated HUVECs, which proved that FpAT can induce apoptosis of HUVECs; and FIG. 9C shows the transcription/expression of apoptosis-related genes/proteins in the levels of RNA transcription and protein expression, which preliminary demonstrated the mechanism of HUVECs apoptosis induced by FpAT.

DETAILED DESCRIPTION OF THE PREFERRED EMBODIMENTS

Figure 1A:
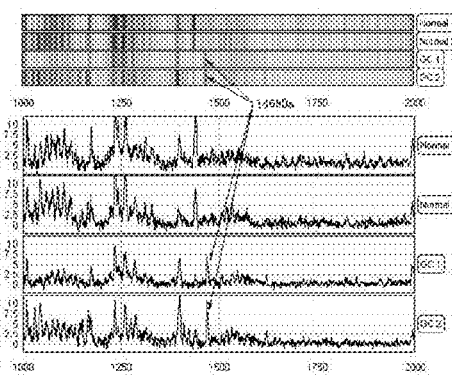

The present invention will be explained in details below by referring to the accompanied drawings, but the present invention is not limited to these specific Examples.

Example 1

Determination of FpAT sequence

Sera of gastric carcinoma patients (127 cases) and normal persons (100 cases) were analyzed by using Surface-Enhanced Laser Desorption/Ionization and Time-of-Flight Mass Spectrometry (SELDI-TOF-MS) technique, protein expression mass spectra of gastric carcinoma serum and non-gastric carcinoma serum were obtained, and through analysis of the model established on artificial neural network, three low molecular weight differential proteins capable of discriminating efficaciously gastric cancer serum from normal serum were screened out. When these three low molecular weight differential proteins together were used as a set of gastric cancer specific markers to diagnose gastric cancer, in the model group the sensitivity and specificity were 95.6% and 92.0% respectively, and the accuracy was 93.7%; and in the blind screen group the sensitivity and specificity were 85.3% and 88% respectively, and the accuracy was 86.4%. One of the low molecular weight differential proteins existed specifically in the serum of gastric cancer patients, and when this low molecular weight differential protein was used alone to perform a diagnosis, in the model group its sensitivity and specificity were 73.3% and 92.0% respectively, and the accuracy was 83.2%; and in the blind screen group its sensitivity and specificity were 67.1% and 100%, and the accuracy was 79.5%, thus it could be seen that this low molecular weight differential protein contribute more to the excellent specificity possessed by the analysis model. Its difference in sera of gastric cancer patients in various phases was further analyzed, and it was found that there was a significant difference between the content in the serum of gastric cancer patients in phase IV and the contents in the sera of gastric cancer patients in phases I~III (P<0.05), and it could be seen that this low molecular weight protein decrease remarkably in the serum of gastric cancer patients in phase IV. The phase IV is characterized mainly in distant metastasis, thus its specific decrease may also prove in another aspect a correlation between its function and tumor metastasis and diffusion. Therefore the inventor speculated preliminarily that FpAT may have an angiogenesis-inhibiting activity and thus be an endogenous angiogenesis inhibitor, which suppresses tumor growth and metastasis mainly through the mechanism of inhibiting the generation of new blood vessels.

The characteristic protein peaks were identified by employing QStar/Pulsar mass spectrometer (Applied Biosystems, Foster City, Calif., USA) and Ciphergen PCI-1000 ProteinChip Interface. According to the conventional analysis steps of SELDI, the serum from a same gastric cancer patient was spotted at eight points on a same SAX2 chip, and one point thereof was analyzed conventionally using SELDI to certify the presence of the peak to be identified, and other points were analyzed employing tandem mass spectrometry technique. And 1468 Da became into smaller molecular ions by collision-induced dissociation in MS-MS, and the fragment peak data was submitted to Mascot protein search engine (Matrix Science, Boston, Mass., USA) to query a most fitting result in known protein and peptide databases.

Figure 1B:
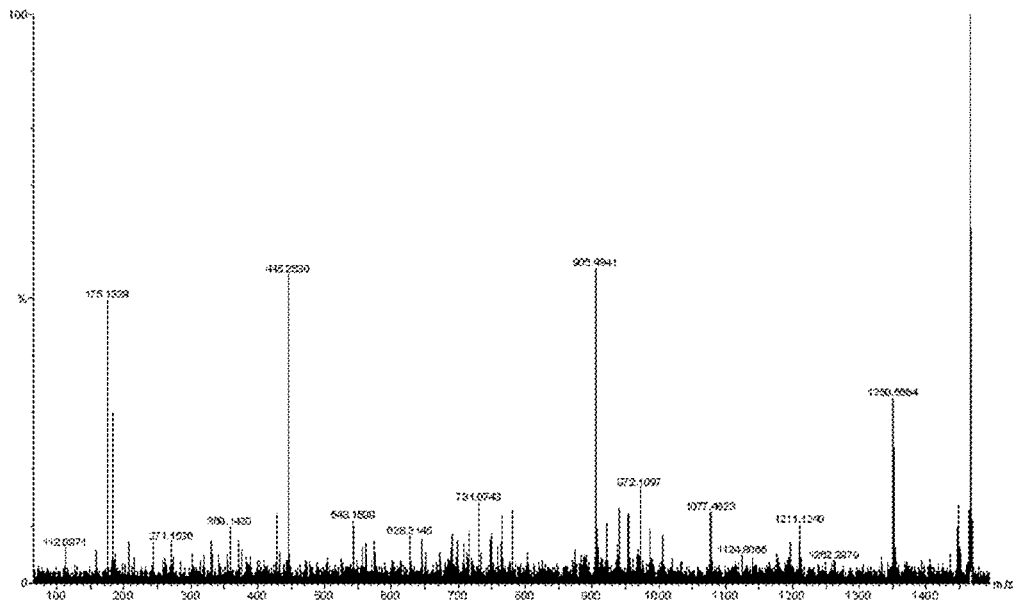

The results were shown in FIG. 1A and FIG. 1B. FIG. 1A illustrated the different distributions of 1468 Da peptide in sera of different populations of gastric carcinoma and normal person control, and this peptide has a significantly higher content in gastric carcinoma patients than normal person control; and FIG. 1B illustrated the fragment peaks of mass spectrometry analysis of the smaller molecular ions converted from 1468 Da by collision-induced dissociation in MS-MS. In conjunction with what shown in Table 3 below, it showed a most fitting result retrieved from known protein and peptide databases after submitting the fragment peak data to Mascot protein search engine (Matrix Science, Boston, Mass., USA), and the sequence result was DSGEGDFLAE-GGGVR (SEQ ID NO: 1), which turned to be fibrinopeptide A fragment (FpA truncated, abbreviated as FpAT) upon database search.

TABLE 3

Sequence of 1468 Da small peptide derived from tandem mass spectrometry analysis

| # | Immon. | b | b0 | Seq. | y | y* | y0 | # |
|---|--------|---|----|------|---|----|----|---|
| 1 | 88.04 | 116.03 | 98.02 | D | | | | 15 |
| 2 | 60.04 | 203.07 | 185.06 | S | 1350.63 | 1333.60 | 1332.62 | 14 |
| 3 | 30.03 | 260.09 | 242.08 | G | 1263.60 | 1246.57 | 1245.59 | 13 |
| 4 | 102.05 | 389.13 | 371.12 | E | 1206.57 | 1189.55 | 1188.56 | 12 |
| 5 | 30.03 | 446.15 | 428.14 | G | 1077.53 | 1060.51 | 1059.52 | 11 |
| 6 | 88.04 | 561.10 | 543.17 | D | 1020.51 | 1003.48 | 1002.50 | 10 |
| 7 | 120.08 | 708.25 | 690.24 | F | 905.48 | 888.46 | 887.47 | 9 |
| 8 | 86.10 | 821.33 | 803.32 | L | 758.42 | 741.39 | 740.40 | 8 |
| 9 | 44.05 | 892.37 | 874.36 | A | 645.33 | 628.30 | 627.32 | 7 |
| 10 | 102.05 | 1021.41 | 1003.40 | E | 574.29 | 557.27 | 556.28 | 6 |
| 11 | 30.03 | 1078.43 | 1062.42 | G | 445.25 | 428.23 | | 5 |
| 12 | 30.03 | 1135.45 | 1117.44 | G | 388.23 | 371.20 | | 4 |
| 13 | 30.03 | 1192.48 | 1174.46 | G | 331.21 | 314.18 | | 3 |
| 14 | 72.08 | 1291.54 | 1273.53 | V | 274.19 | 257.16 | | 2 |
| 15 | 129.11 | | | R | 175.12 | 158.09 | | 1 |

Example 2

Chemical Synthesis of FpAT Peptide and Derivative Peptides Thereof (see Table 2 for Specific Sequences)

Chemical synthesis of FpAT peptide ($H_2N$-Asp-Ser-Gly-Glu-Gly-Asp-Phe-Leu-Ala-Glu-Gly-Gly-Gly-Val-Arg-COOH) (SEQ ID NO: 1):

A peptide synthesis column packed with 4-(2',4'-dimethoxyphenyl-Fmoc-aminomethyl) phenoxy acetyl amino ethyl resin was placed in Pioneer™ peptide synthesizer, and the peptide synthesis was performed in nitrogen gas in an order below:

1. the resin was solvated in DMF for 5 minutes;
2. the resin was treated by 20% piperidine in DMF for about 15 minutes, and the protective group Fmoc on the grafted group of the resin (or on the α-amino group of amino acid bonded with the resin) was removed;
3. the resin was washed with DMF for 5 minutes;
4. α-carboxyl group of the first amino acid Arg at C-terminal was activated with a solution of 0.2M HBTU and 0.2M HOBT in DMSO-NMP (N-methylpyrrolidone) and a solution of 0.4M diisopropyl ethyl amine in DMSO-NMP;
5. the activated amino acid obtained in step 4 was coupled with the resin (or an amino acid bonded to resin) of step 2 in DMF for about 30 minutes;
6. the resin was washed with DMF for 5 minutes;
7. the step 2 to 6 were repeated with the following amino acids: Fmoc-Val, Fmoc-Gly, Fmoc-Gly, Fmoc-Gly, Fmoc-Glu (γ-0tBu), Fmoc-Ala, Fmoc-Leu, Fmoc-Phe, Fmoc-Asp (β-0tBu), Fmoc-Gly, Fmoc-Glu (γ-0tBu), Fmoc-Gly, Fmoc-Ser (tBu), Fmoc-Asp (β-0tBu);
8. the resin was washed with THF for about 5 minutes;
9. the resin was agitated with newly prepared mixed cutting reagent thioanisole:water:dimercapto ethane:trifluoroacetic acid (2:1:1:36, by volume) at 0° C. for 10 to 15 minutes, and then agitated at room temperature for 2 hours;
10. a filtration was performed and the filtrate was centrifuged in cold diethyl ether; the supernatant was poured out and the centrifugation in cold diethyl ether was repeated until the peptides completely precipitate; the rough peptide product thus obtained was purified chromatographically on a C18 silica gel preparative column, eluted gradiently with acetonitrile/(water, 0.1% TFA); the eluted fractions containing target peptide were collected and lyophilized, and 50 mg FpAT peptide was obtained.

Chemical synthesis of FpAT-N3d peptide ($H_2N$-Glu-Gly-Asp-Phe-Leu-Ala-Glu-Gly-Gly-Gly-Val-Arg-COOH) (SEQ ID NO: 2): FpAT-N3d peptide (12 mers, corresponding to FpAT peptide with 3 amino acids at N-terminal deleted) was synthesized in the same manner as above from C-terminal to N-terminal;

Chemical synthesis of FpAT-N6d peptide ($H_2N$-Phe-Leu-Ala-Glu-Gly-Gly-Gly-Val-Arg-COOH) (SEQ ID NO: 3): FpAT-N6d peptide (9 mers, corresponding to FpAT peptide with 6 amino acids at N-terminal deleted) was synthesized in the same manner as above from C-terminal to N-terminal;

Chemical synthesis of FpAT-N9d peptide ($H_2N$-Glu-Gly-Gly-Gly-Val-Arg-COOH) (SEQ ID NO: 4): FpAT-N9d peptide (6 mers, corresponding to FpAT peptide with 9 amino acids at N-terminal deleted) was synthesized in the same manner as above from C-terminal to N-terminal;

Chemical synthesis of FpAT-C3d peptide ($H_2N$-Asp-Ser-Gly-Glu-Gly-Asp-Phe-Leu-Ala-Glu-Gly-Gly-COOH) (SEQ ID NO: 5): FpAT-C3d peptide (12 mers, corresponding to FpAT peptide 1 with 3 amino acids at C-terminal deleted) was synthesized in the same manner as above from C-terminal to N-terminal;

Chemical synthesis of FpAT-C6d peptide (H₂N-Asp-Ser-Gly-Glu-Gly-Asp-Phe-Leu-Ala-COOH) (SEQ ID NO: 6): FpAT-C6d peptide (9 mers, corresponding to FpAT peptide with 6 amino acids at C-terminal deleted) was synthesized in the same manner as above from C-terminal to N-terminal;

Chemical synthesis of FpAT-C9d peptide (H₂N-Asp-Ser-Gly-Glu-Gly-Asp-COOH) (SEQ ID NO: 7): FpAT-C9d peptide (6 mers, corresponding to FpAT peptide with 9 amino acids at C-terminal deleted) was synthesized in the same manner as above from C-terminal to N-terminal;

Chemical synthesis of FpAT-N6d-C3d peptide (H₂N-Phe-Leu-Ala-Glu-Gly-Gly-COOH) (SEQ ID NO: 16), FpAT-N6d-C3d peptide (6 mers, corresponding to FpAT peptide with 6 amino acids at N-terminal and 3 amino acids at C-terminal deleted) was synthesized in the same manner as above from C-terminal to N-terminal;

Chemical synthesis of FpAT-N7d-C3d peptide (H₂N-Leu-Ala-Glu-Gly-Gly-COOH) (SEQ ID NO: 15), FpAT-N7d-C3d peptide (5 mers, corresponding to FpAT peptide with 7 amino acids at N-terminal and 3 amino acids at C-terminal deleted) was synthesized in the same manner as above from C-terminal to N-terminal;

Chemical synthesis of FpAT-N7d-C2d peptide (H₂N-Leu-Ala-Glu-Gly-Gly-Gly-COOH) (SEQ ID NO: 13), FpAT-N7d-C2d peptide (6 mers, corresponding to FpAT peptide with 7 amino acids at N-terminal and 2 amino acids at C-terminal deleted) was synthesized in the same manner as above from C-terminal to N-terminal;

Chemical synthesis of FpAT-N5d-C4d peptide (H₂N-Asp-Phe-Leu-Ala-Glu-Gly-COOH) (SEQ ID NO: 8), FpAT-N5d-C4d peptide (6 mers, corresponding to FpAT peptide with 5 amino acids at N-terminal and 4 amino acids at C-terminal deleted) was synthesized in the same manner as above from C-terminal to N-terminal.

Example 3

Homology Analysis of FpAT and VEGF

Using analysis program (www.ebi.ac.uk/Tools/Sequence Analysis-ClustalW), a sequence alignment analysis of the homology of FpAT with VEGF was carried out according to the default parameters, and below is the analysis result:

```
FpAT       -----DSG-------------EG--------DFL----------------   8
(SEQ ID    RRGAEESGPPHSPSRRGSASRAGPGRASETMNFLLSWVHWSLALLLYLHH 200
NO: 1          :**                *          :**

VEGF       ---------AEGGG------VR----------------------------  15
(SEQ ID    AKWSQAAPMAEGGGQNGGEVVKFMDVYQRSYCHPIETLVDIFQEYPDEIE 250
NO: 17              *****        *:
```

It could be seen that the six amino acids Leu-Ala-Glu-Gly-Gly-Gly (SEQ ID NO: 13) thereof, at least the five amino acids Ala-Glu-Gly-Gly-Gly (SEQ ID NO: 14) thereof are the important sequence of this peptide.

Example 4

Suppression of Tumor Growth in Mice of Kunming Strain by FpAT In Vivo

To confirm the biological effects of FpAT on the growth of mice deriving tumor in mice in vivo, a tumor suppression experiment was carried out in this example using liver cancer H22 cells tumor-bearing mouse model of mice of Kunming strain and osteosarcoma S180 cells tumor-bearing mouse model of mice of Kunming strain.

Forty 5-week old mice of Kunming strain purchased from Animal Center Of Chinese Academy Of Medical Sciences were inoculated subcutaneously in forelimb with mouse liver cancer H22 cells (National Institute for the Control of Pharmaceutical and Biological Products) ($5 \times 10^6/100$ μl/mouse) or osteosarcoma S180 cells (National Institute for the Control of Pharmaceutical and Biological Products) ($5 \times 10^6/100$ μl/mouse). On the next day after inoculation, each kind of inoculated cells were divided into 2 groups randomly with 10 mice per group. FpAT (50 m/1000 PBS/injection) or vehicle (the solvent for peptide) control (PBS:100 μl/injection) were injected in angulus oculi medialis vein daily, 7 times in total. The mice were sacrificed by dislocating the neck on the next day after administration was stopped, and the tumors were taken and weighed for a statistical analysis.

Figure 2A:
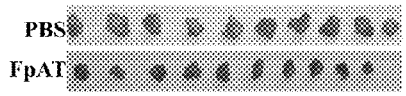
Figure 2B:

The results were shown in FIG. 2A and FIG. 2B. FpAT could suppressed the growths of mouse liver cancer H22 cells and osteosarcoma S180 cells in the mice of Kunming strain in vivo, and delayed the rate of tumor growth: as shown by the statistical analysis (using two-sample t-test), the tumor mass from the administered group were small generally, which differed significantly from the PBS control group ($P<0.05$).

Example 5

Suppression of Tumor Growth in Nude Mice In Vivo by FpAT

In order to confirm the biological effects of FpAT on the growth of human deriving tumors in nude mice in vivo, a tumor suppression experiment was carried out in this example using human gastric carcinoma BGC-823 cells tumor-bearing nude mice model, human lung cancer PG cells tumor-bearing nude mice model and human colon cancer HT-29 cells tumor-bearing nude mice model.

Twenty 5-week old Balb/c nude mice purchased from Animal Center Of Chinese Academy Of Medical Sciences were inoculated subcutaneously in forelimb with human gastric carcinoma BGC-823 cells (National Institute for the Control of Pharmaceutical and Biological Products) ($5 \times 10^6/100$ μl/mouse), human lung cancer PG cells (National Institute for the Control of Pharmaceutical and Biological Products) ($5 \times 10^6/100$ μl/mouse) or human colon cancer HT-29 cells (ATCC® Number: HTB-38™) ($5 \times 10^6/100$ μl/mouse). On the next day after inoculation, each kind of inoculated cells were divided into 2 groups randomly with 5 mice per group. FpAT (50 μg/100 μl PBS/injection) or vehicle control (PBS: 100 μl/injection) were injected in angulus oculi medialis vein once every other day, 10 times in total. Observation was continued for another 20 days after administration was stopped, and during this period the long and short diameters of the tumors were measured with a vernier caliper once every three days, and the volumes of the tumor mass were calculated according to formula ½×long diameter×short diameter². 20 days after administration was stopped, the mice were sacrificed by dislocating the neck, and the tumors were taken and weighed for a statistical analysis.

Figure 3A:
Figure 3B:
Figure 3C:

The results were shown in FIG. 3A, FIG. 3B and FIG. 3C. FpAT could suppress the growths of human gastric carcinoma BGC-823 cells, human lung cancer PG cells and human colon cancer HT-29 cells in the nude mice in vivo, and delayed the rate of tumor growth: as shown by the statistical analysis (using two-sample t-test), the tumor mass of the administered group were small generally, which differed significantly from the vehicle group ($P<0.05$).

Example 6

Effects of FpAT on the Tumor Microvessel Density in Mice In Vivo

In order to confirm that the suppression of FpAT on tumor growth in mice in vivo is achieved by suppressing angiogenesis, an analysis of microvessel density in tumor was performed in this example by using tumor mass in Examples 4 and 5.

The tumor masses were fixed with formaldehyde, and then cut into serial section of 3 μm. The paraffin sections were dewaxed to water, and incubated in 3% $H_2O_2$ at room temperature for 10 minutes, to which rabbit anti-human factor VIII polyclonal antibody (DAKO company) was added dropwise, and after left at 4° C. overnight; 1:200 sheep anti-rabbit IgG labeled with biotin (Beijing ZhongShan bioengineering Company) was added dropwise, and incubated at 37° C. for 30 minutes. Then DAB (Beijing ZhongShan bioengineering Company) was used to develop for 5 minutes. Rabbit IgG was used in place of the first antibody as the blank control, and hemangioma was used as the positive control. Firstly the staining of micro blood vessel was checked under low magnitude field to avoid necrosis and inflammation sites, and new blood vessel endothelium stained into a brownish yellow color was taken as the determining standard of positivity. Then a visual field with most interstitial blood vessels of cancer nest was chosen, and under a ×400 magnitude field, 3 visual fields were counted by 3 observers individually according to double blind method; wherein individual cells and cell clusters stained brown were observed and taken as one blood vessel, whereas blood vessel cavities and erythrocytes therein were not counted, and blood vessel or vessel cavities in muscular layer larger than 50 μm were excluded. The average value of numbers counted by 3 individuals was taken as MVD (microvessel density) result of this case for a statistics analysis, see Table 4.

TABLE 4

Effect of FpAT on tumor microvessel density in mice in vivo

| Number of micro vessel/visual field[#] | PBS group | FpAT group |
|---|---|---|
| MVD | 6.4 | 2.6 |

[#]20 visual fields observed totally

Figure 4:
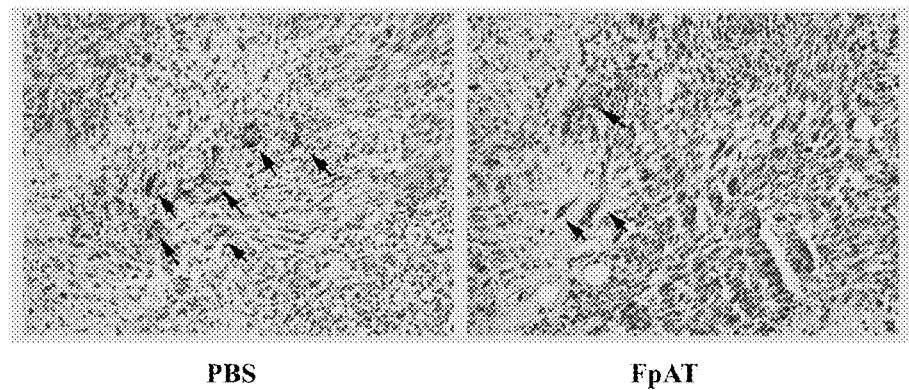
FIG. 4 shows the effects of FpAT on density of blood vessel in mice tumor in vivo.

The results were shown in FIG. 4. FpAT suppressed significantly the growth of microvessel in tumor issue: as shown by the statistical analysis (using two-sample t-test), the microvessel density in tumor mass of the administered group was much smaller, which differed significantly from PBS control group ($P<0.05$).

Example 7

Suppression of Proliferation of Chick Chorioallantoic Membrane Vessel by FpAT

In this example an experiment of proliferation of chick chorioallantoic membrane vessel was carried out to test suppressing effects of FpAT on angiogenesis.

The test was performed according to the method described in the reference "Fu Shengfa, Lu yinglin, Zhang Chaoshan et al., A chick chorioallantoic membrane technique to test function of vascular growth factors, Bulletin of the Academy of Military Medical Sciences 1993, 17:294-97". Fresh fertilized hen eggs were immersed into 0.1% benzalkonium bromide solution at 38° C. for 2 minutes, and then incubated in an incubator at 37.5° C. in a humidity of 60-70% for 3 days. Then the eggs with shell removed were transferred to plate and cultured. The samples were separated into groups and administered when the allantoic membrane grew to about 2 cm², 5 chicken embryos per group. 10 μl of FpAT (1 μg/μL), PBS (negative control) was dropped on a glass fiber filter membrane of Φ4 mm, which was placed at distal end of chorioallantoic membrane, and cultured for 24 hours. The results were observed and recorded by taking photos. The experiment was repeated twice.

Figure 5:
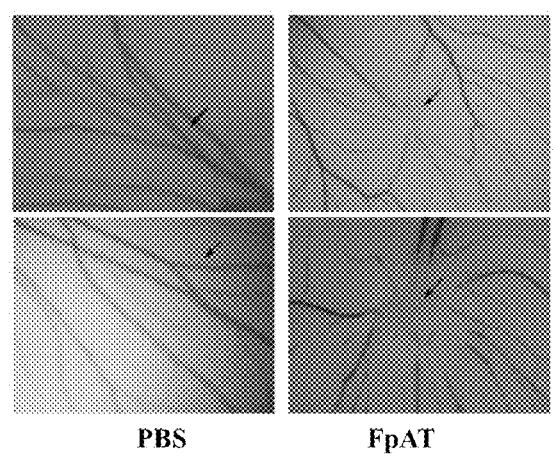
FIG. 5 shows that FpAT inhibits proliferation of blood vessel of chick chorioallantoic membrane.

The results were shown in FIG. 5. It was shown that FpAT are capable of not only suppressing remarkably blood vessel formation but also inducing disorder of blood vessel distribution and atrophy of original blood vessel. This demonstrated that FpAT has a biological activity of inhibiting angiogenesis (sites indicated by arrows were those administered by glass fiber filter membrane, and PBS group has no inhibiting effects on growth of vessel, whereas FpAT is capable of not only suppressing remarkably blood vessel formation but also inducing disorder of blood vessel distribution and atrophy of original blood vessel).

Example 8

Effects of FpAT on Growth of Endothelial Cell of Mouse Aorta

To further investigate the effects of FpAT on growth of vascular endothelial cell, the effects of FpAT on the growth of primary endothelial cells of mouse aorta in vitro were observed in this example.

The Balb/c mice were sacrificed by dislocating the neck and aorta were detached and washed off the blood cells therein with PBS. The cleaned aorta was cut into aorta segments in length of 1 mm, which were planted vertically in 24-well cell culture plate coated with Matrigel gel (BD company); and 10% FCS/RPMI1640 was added, and the plates were placed and cultured in $CO_2$ incubator (37° C., 5% $CO_2$). The vehicle (PBS) and FpAT (10 μg/ml PBS, 25 μg/ml PBS, 100 μg/ml PBS) were added separately, with 3 parallel wells per group, and the cultivation was performed for 48 hours, 72 hours. Then the growth of mouse aorta endothelial cell was observed under microscope.

Figure 6:
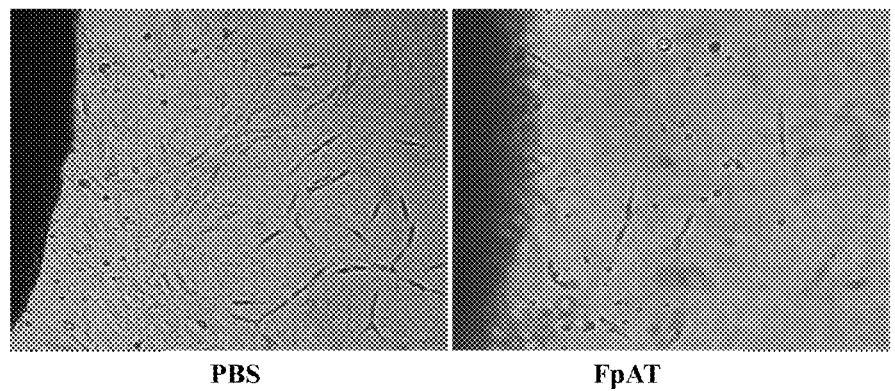
FIG. 6 shows that FpAT inhibits growth, migration and ability to form tubular structure of endothelial cells of mouse aorta.

The results were shown in FIG. 6, which illustrated that FpAT can suppress specifically the growth of vascular endothelial cell of mouse aorta, and suppress notably the proliferation, migration and ability to form tubular structure of vascular endothelial cell of mouse aorta.

Example 9

FpAT can not Suppress the Proliferation of Mouse Breast Carcinoma Cell D2F2 Cells In Vitro To investigate direct effects of FpAT on tumor cells in vitro, the influence of FpAT on the proliferation of D2F2 cell (Balb/c mouse-derived breast carcinoma cell) was examined using MTT in this example.

D2F2 cells (Mahoney K H, Miller B E, Heppner G H. FACS quantitation of leucine aminopeptidase and acid phosphatase on tumor-associated macrophages from metastatic and nonmetastatic mouse mammary tumors. J Leukoc Biol. 1985 November; 38(5): 573-85.) were cultured conventionally. The cultured D2F2 cells were digested with 0.04% trypsin-EDTA, and inoculated into 96-well plate at $3 \times 10^3$ cells/well; after 24 hours of culture, PBS and FpAT (25 µg/ml PBS) were added separately, with 4 parallel wells per group. Ninety six hours later, 20 µl MTT solution of mass concentration of 5 mg/ml was added to each well. After the culture was performed continuously for 4 hours, the original culture medium was discarded and 200 µl DMSO was added to each well, and then it was shaken for 15 minutes. After mixed well, OD value (measured at a wavelength of 570 nm) of each well was measured in a microplate reader, and the cell suppression rates were calculated according to the following formula: cell suppression rate=(mean OD value of blank control group−mean OD value of treated group)/mean OD value of blank control group×100%.

Figure 7:
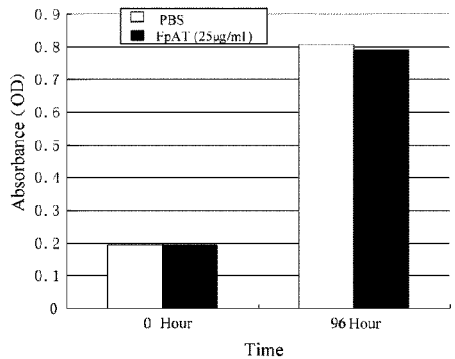
FIG. 7 shows that FpAT can not inhibit proliferation of D2F2 cells in vitro.

The results were shown in FIG. 7, which illustrated that FpAT can not suppress D2F2 cells in vitro, indicating that FpAT can not suppress the proliferating activity of tumor cells.

Example 10

Specific Suppression of FpAT on the Proliferation of Vascular Endothelial Cell In order to further investigate the effects of FpAT on the proliferation of various vascular endothelial cells, a cell proliferation suppression experiment was carried out using MTT method in this example.

Human umbilical cord samples (obtained from Beijing Obstetrics & Gynecology Hospital) was digested with 0.1% collagenase I (available from GIBCO BRL company), followed by a centrifugation (1000 rpm, 10 minutes) to collect human umbilical vein endothelial cells (HUVECs). After suspended in 20% FCS/RPMI1640, the cells were transferred into plastic bottles for culture in $CO_2$ incubator (37° C., 5% $CO_2$). Twelve hours later, unattached cells were discarded by changing medium, and then the remaining cells were cultured conventionally with the medium changed every 3 days. The cultured HUVECs were digested with 0.04% trypsin-EDTA, and inoculated into 96-well plate at $2 \times 10^3$ cells/well. After 24 hours of culture, the vehicle (PBS) and FpAT (25 µg/ml PBS) were added separately, with 4 parallel wells per group. 20 µl MTT solution of mass concentration of 5 mg/ml was added to each well at 24, 48, 72, 96 hours. After the culture was performed continuously for 4 hours, the original culture medium was discarded and 200 µl DMSO was added to each well, and then it was shaken for 15 minutes. After mixed well, OD value (measured at a wavelength of 570 nm) of each well was measured in a microplate reader, and the cell suppression rates were calculated according to the following formula: cell suppression rate=(mean OD value of blank control group-mean OD value of treated group)/mean OD value of blank control group×100%.

Figure 8:
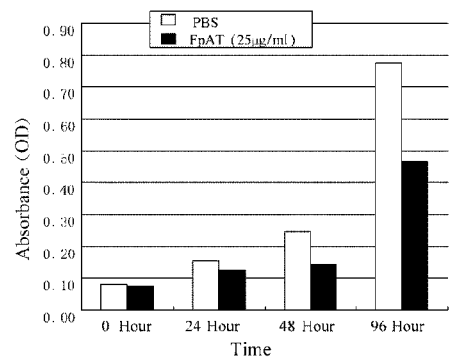
FIG. 8 shows that FpAT inhibits specifically proliferation of HUVECs (human umbilical vein endothelial cells).

The results were shown in FIG. 8, which illustrated that FpAT can specifically suppress the proliferation of vascular endothelial cell (human umbilical vein endothelial cells) by the suppressing rate of 40.1%.

A similar experiment was performed except that the human umbilical vein endothelial cells (HUVECs) were replaced with pig aorta endothelial cells (PAEC) by the applicant, and also came to a same conclusion.

Example 11

The Apoptosis of Vascular Endothelial Cell Induced by FpAT

To investigate the effects of FpAT on induction of the apoptosis of vascular endothelial cell, the effects of FpAT on the apoptosis of human umbilical vein endothelial cells were observed in three levels of cell, RNA, and protein by using Flow Cytometry method and RT-PCR and Western blotting in this example.

Human umbilical cord samples (obtained from Beijing Obstetrics & Gynecology Hospital) was digested with 0.1% collagenase I (available from GIBCO BRL company), followed by a centrifugation (1000 rpm, 10 minutes) to collect human umbilical vein endothelial cells (HUVECs). After suspended in 20% FCS/RPMI1640, the cells were transferred into plastic bottles for culture in $CO_2$ incubator (37° C., 5% $CO_2$). Twelve hours later, unattached cells were discarded by changing medium, and then the remaining cells were cultured conventionally with the medium changed every 3 days. The vehicle (PBS) and FpAT (50 µg/ml PBS) were added separately, and the cells were collected at 96 hours. [1] Flow Cytometry: the cells were digested with 0.04% trypsin-EDTA, collected and washed 3 times with PBS; the cells were suspended by adding 200 µl PBS and aspirated gently to avoid formation of cell mass. 800 µl cold absolute alcohol was added, and then the cells was fixed at 4° C. overnight; and after a centrifugation at 1000×g for 5 min at 4° C., and the supernatant were discarded. The cells were washed twice with PBS, re-suspended with 200 µl PBS containing RNaseA at a concentration of 1 mg/ml, and incubated at 37° C. for 30 minutes. PI staining solution (final concentration of 50 µg/ml) was added, and the well mixed cells were subjected to a reaction at 4° C. for 30 minutes in the dark. The detection was performed on a flow cytometer. [2] DNA Ladder analysis: the cells differently treated (PBS and FpAT) were collected by a centrifugation at 1000 rpm for 5 minutes, and the cells were lysed with lysis solution (10 mM Tris-HCl, 5 mM EDTA, 1% Triton-X 100, 10 mM NaCl, 100 µg/ml protease K), and aspirated repeatedly to cut viscous genomic DNA, which theoretically generates DNA fragments in a uniform size of 20 to 30 kb; phenols and chloroform were used to extract, and after precipitated with absolute ethanol, the total DNA were dissolved in TE or water, and treated with Rnase A at 37° C. for 1~2 hours. Five microliters was taken for an electrophoresis on 1.8% agarose gel. [3] RT-PCR analysis: cells differently treated (PBS and FpAT) were digested, and total RNA was extracted according to Trizol kit (available from Invitrogen Company) method. The total RNA was reverse-transcripted into cDNA according to Reverse Transcription System (available from Promega Company) method. Primers of Bcl-2, Bax, Bad, Bcl-xL, Caspase-3, P53, GAPDH were designed respectively, and Bcl-2, Bax, Bad, Caspase-3, P53 were amplified by PCR with GAPDH as internal reference. Five microliters of amplified products was taken and subjected to an electrophoresis on 1.2% agarose gel to observe the RNA transcription levels of corresponding genes in the cells differently treated (PBS and FpAT). [4] Western blotting analysis: cells differently treated (PBS and FpAT) were digested and total protein was extracted according to Trizol kit (available from Invitrogen Company) method. A SDS-PAGE electrophoresis was performed, and the proteins in the SDS-PAGE gel were electro-transferred onto a nitrocellulose membrane. Expression levels of corresponding proteins of the cells differently treated (PBS and FpAT) were observed by performing a conventional Western blotting analysis, using antibodies against corresponding protein, i.e. an antibody against bcl-2 (available from Santa Cruz Company, sc-7382), an antibody against bax (available from Santa Cruz Company, sc-7480), an antibody against caspase-3 (available from Santa Cruz Company, sc-7272), an antibody against p53 (available from Santa Cruz Company, sc-126) as primary antibody, and β-actin (available from ABCAM Company, ab-3280) as internal reference control.

Figure 9A:
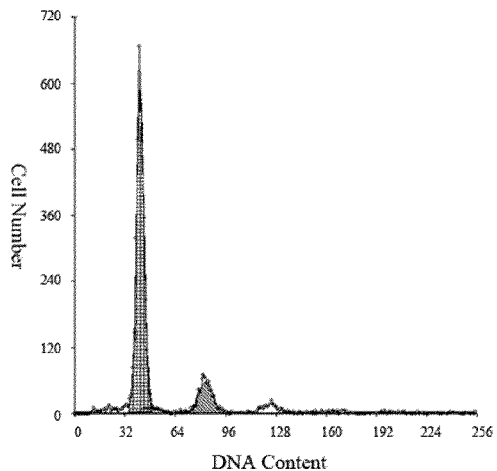
Figure 9A:
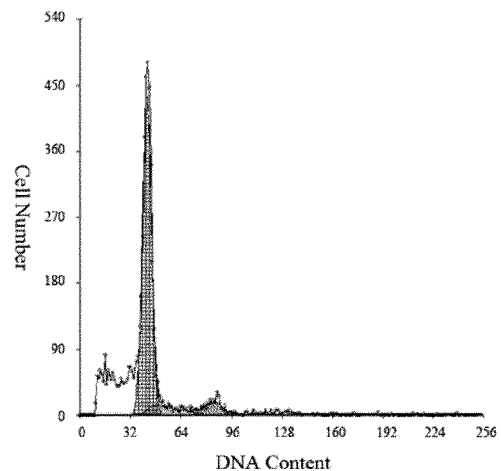
Figure 9B:
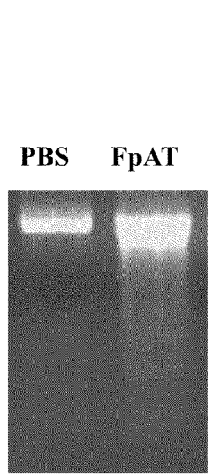
Figure 9C:
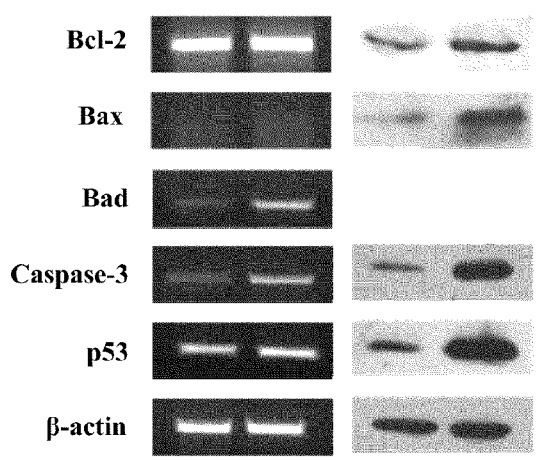

The results were shown in FIG. 9A, FIG. 9B and FIG. 9C, which proved that apoptosis of human umbilical vein endothelial cells can be induced by FpAT at three levels of cell, RNA, protein. Among the figures, FIG. 9A showed that FpAT has no remarkable effects on cell cycle of HUVECs (human umbilical vein endothelial cells), but the presence of an evidence apoptosis peak was found by flow cytometry analysis, demonstrating that FpAT can induce apoptosis of HUVECs; FIG. 9B showed that the presence of plenty of DNA Ladder in total DNA extracted from FpAT treated HUVECs, demonstrating that FpAT can induce apoptosis of HUVECs; FIG. 9C showed the transcription/expression of apoptosis related genes/proteins in the levels of RNA transcription and protein expression, preliminary demonstrating the mechanism of HUVEC apoptosis induced by FpAT.

Example 12

Specific Suppression on the Ability to Form a Tubular Structure of Vascular Endothelial Cell by FpAT In order to investigate the effects of FpAT on the ability to form a three-dimensional and tubular structure of vascular endothelial cell, the effects of FpAT on the ability to form a three-dimensional and tubular structure of human umbilical vein endothelial cells were observed in vitro in this Example.

Human umbilical cord samples (obtained from Beijing Obstetrics & Gynecology Hospital) was digested with 0.1% collagenase I (available from GIBCO BRL company), followed by a centrifugation (1000 rpm, 10 minutes) to collect human umbilical vein endothelial cells (HUVECs). After suspended in 20% FCS/RPMI1640, the cells were transferred into plastic bottles for culture in $CO_2$ incubator (37° C., 5% $CO_2$). Twelve hours later, unattached cells were discarded by changing medium, and then the remaining cells were cultured conventionally with the medium changed every 3 days. The cultured HUVECs were digested with 0.04% trypsin-EDTA, and inoculated into 24-well plate at $2\times10^4$ cells/well; and the vehicle (PBS) and FpAT (10 μg/ml PBS, 25 μg/ml PBS, 100 μg/ml PBS) were added separately, with 3 parallel wells per group. The growth of HUVECs was observed at 48, 72, 96 hours under microscope.

Figure 10:
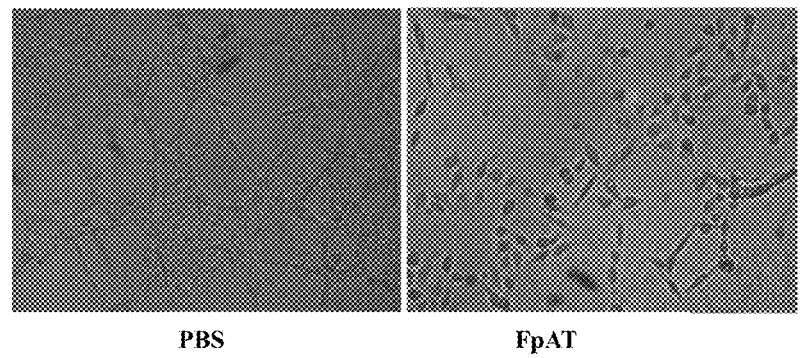
FIG. 10 shows that FpAT can suppress the ability of HUVECs (human umbilical vein endothelial cells) to form three-dimensional tubular structure.

The results were shown in FIG. 10, which illustrated that FpAT can suppress specifically the ability to form a three-dimensional and tubular structure of human umbilical vein endothelial cells.

Example 13

Microfilament Disassembly of Vascular Endothelial Cell Induced by FpAT

In order to investigate the effects of FpAT on the skeleton of vascular endothelial cells, the effect of FpAT on the microfilamental skeleton of human umbilical vein endothelial cells were observed in vitro in this example.

Human umbilical cord samples (obtained from Beijing Obstetrics & Gynecology Hospital) was digested with 0.1% collagenase I (available from GIBCO BRL company), followed by a centrifugation (1000 rpm, 10 minutes) to collect human umbilical vein endothelial cells (HUVECs). After suspended in 20% FCS/RPMI1640, the cells were transferred into plastic bottles for culture in $CO_2$ incubator (37° C., 5% $CO_2$). Twelve hours later, unattached cells were discarded by changing medium, and then the remaining cells were cultured conventionally with the medium changed every 3 days. The cultured HUVECs were digested with 0.04% trypsin-EDTA, and inoculated into 24-well plate at $2\times10^4$ cells/well; and the vehicle (PBS) and FpAT (10 μg/ml, 25 μg/ml, 100 μg/ml) were added separately, with 3 parallel wells per group. The growth of HUVECs was observed at 48, 72, 96 hours under a microscope. After washing twice with PBS, Hoechst was added to stain nucleus. After washed once with PBS, the slide was mounted with mounting solution, and stored at 4° C. in the dark. The change of cytoskeleton was observed employing a confocal microscope.

Figure 11:
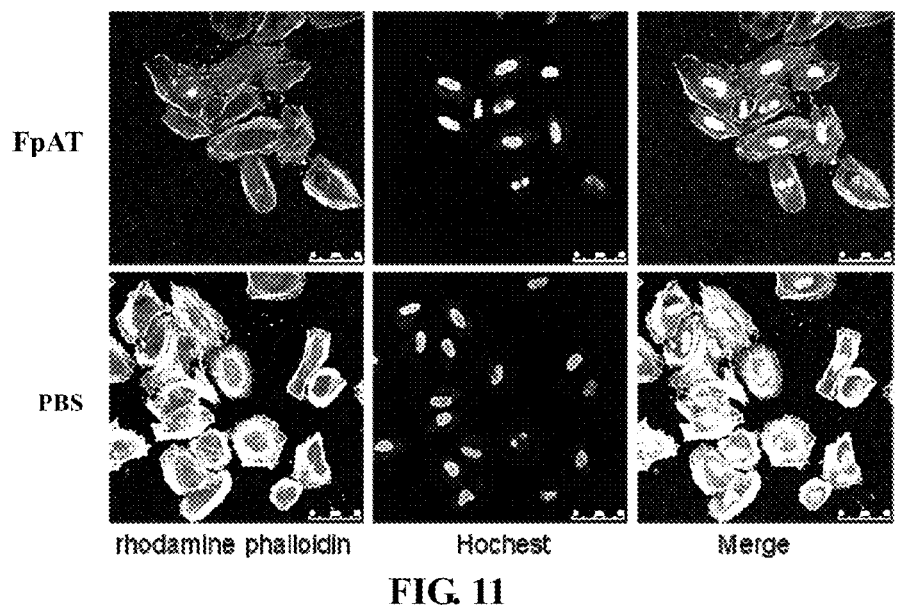
FIG. 11 shows that FpAT can induce disassembly of microfilament in HUVECs (human umbilical vein endothelial cells).

The results were shown in FIG. 11, which illustrated that FpAT can induce the microfilament disassembly in HUVECs (human umbilical vein endothelial cells).

Example 14

Suppression by FpAT and Derivative Peptides Thereof on Tumor Growth in Mice of Kunming Strain In Vivo In order to confirm the biological effects of FpAT and various derivative peptides thereof on the growth of mouse-derived tumor in mice in vivo, a tumor suppression experiment was carried out in this example by using liver cancer H22 cells tumor-bearing mouse model of mice of Kunming strain.

Ninety 5-week old mice of Kunming strain purchased from Animal Center Of Chinese Academy Of Medical Sciences were inoculated subcutaneously in forelimb with mice liver cancer H22 cells (National Institute for the Control of Pharmaceutical and Biological Products) ($5\times10^6$/100 μl/mouse). On the next day after inoculation, each kind of inoculated cells were divided randomly into 9 groups with 10 mice per group. FpAT (50 μg/100 μl PBS/injection) and 7 kinds of derivative peptides thereof (see Table 5 below for detailed sequence):FpAT-N3d, FpAT-N6d, FpAT-N9d, FpAT-C3d, FpAT-C6d, FpAT-C9d, FpAT-N5d-C4d, and vehicle control (PBS:100 μl/injection) were injected in angulus oculi medialis vein, with CTX (cyclophosphamide) (80 mg/KG) as positive control daily, 7 times in total. The mice were sacrificed by dislocating the neck on the next day after administration was stopped, and the tumors were taken and weighed for a statistical analysis.

Figure 12:
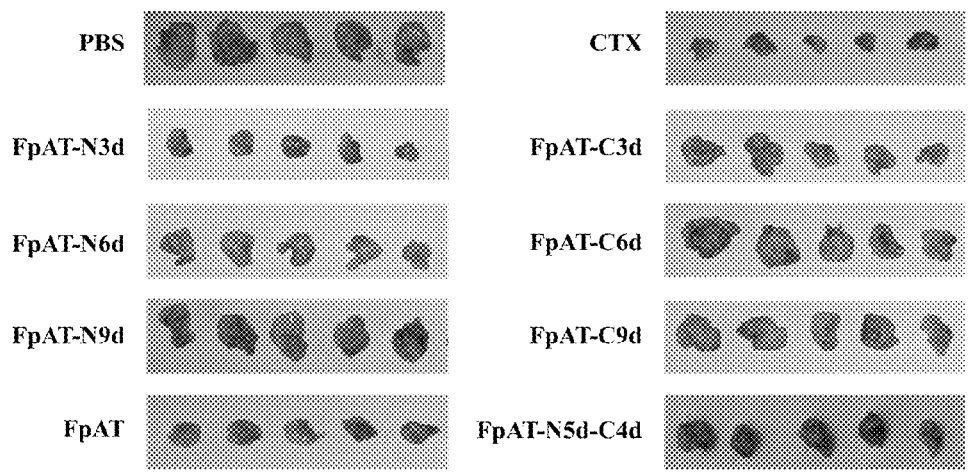
FIG. 12 shows the suppression of tumor (liver cancer H22) growth in mice of Kunming strain in vivo by FpAT and derivative peptides thereof.

The results were shown in FIG. 12, which demonstrated that FpAT and derivative peptides thereof can suppress at different extent the growth of mice liver cancer H22 cells in the mice of Kunming strain in vivo, and delay the tumor growth rate: as shown by the statistical analysis (using two-sample t-test), the tumor mass of the administered group were small generally, which differed significantly from the vehicle group ($P<0.05$).

Furthermore, the peptides were ranked according to the value of tumor suppressing rates, and the ranked results were shown in Table 5 below:

TABLE 5

Ranked results according to the value of tumor suppressing rate

| Small peptide | Sequences | tumor suppressing rate |
|---|---|---|
| CTX | | 89.9% |
| FpAT | Asp-Ser-Gly-Glu-Gly-Asp-Phe-Leu-Ala-Glu-Gly-Gly-Gly-Val-Arg (SEQ ID NO: 1) | 65.4% |
| FpAT-N3d | Glu-Gly-Asp-Phe-Leu-Ala-Glu-Gly-Gly-Gly-Val-Arg (SEQ ID NO: 2) | 63.3% |
| FpAT-N6d | Phe-Leu-Ala-Glu-Gly-Gly-Gly-Val-Arg (SEQ ID NO: 3) | 57.6% |
| FpAT-N5d-C4d | Asp-Phe-Leu-Ala-Glu-Gly (SEQ ID NO: 8) | 56.4% |
| FpAT-C3d | Asp-Ser-Gly-Glu-Gly-Asp-Phe-Leu-Ala-Glu-Gly-Gly (SEQ ID NO: 5) | 46.7% |
| FpAT-N9d | Glu-Gly-Gly-Gly-Val-Arg (SEQ ID NO: 4) | 34.5% |
| FpAT-C9d | Asp-Ser-Gly-Glu-Gly-Asp (SEQ ID NO: 7) | 34.5% |
| FpAT-C6d | Asp-Ser-Gly-Glu-Gly-Asp-Phe-Leu-Ala (SEQ ID NO: 6) | 32.3% |

It could be seen from the results above that both FpAT of the present invention and derivative peptides thereof can suppress efficaciously the tumor growth in mice of Kunming strain in vivo, and among them the peptides containing six successive amino acids of Asp-Phe-Leu-Ala-Glu-Gly (SEQ ID NO: 8) are significantly different from the peptides not containing these six amino acids in tumor suppressing rate ($P<0.05$). Therefore, the inventor considered preliminarily that the six successive amino acids of Asp-Phe-Leu-Ala-Glu-Gly (SEQ ID NO: 8) are the important sequence of the peptide of the present invention.

---

The invention claimed is:

1. A peptide consisting of SEQ ID NO: 5, SEQ ID NO: 6, SEQ ID NO: 7, or SEQ ID NO: 8, or a pharmaceutically acceptable salt of said peptide.

2. The peptide or pharmaceutically acceptable salt of the peptide according to claim 1, wherein the peptide consists of SEQ ID NO: 6.

3. The peptide or pharmaceutically acceptable salt of the peptide according to claim 1, wherein the peptide consists of SEQ ID NO: 8.

4. The peptide or pharmaceutically acceptable salt of the peptide according to claim 1, wherein the peptide consists of SEQ ID NO: 5.

5. The peptide or pharmaceutically acceptable salt of the peptide according to claim 1, wherein the peptide consists of SEQ ID NO:7.

6. A composition for treating an angiogenesis disease or preventing a postoperative tumor recurrence or metastasis, the composition comprising a peptide or a pharmaceutically acceptable salt thereof, wherein the peptide consists of SEQ ID NO: 5, SEQ ID NO: 6, SEQ ID NO: 7, or SEQ ID NO: 8.

7. The composition of claim 6, wherein the tumor is a solid tumor.

8. A pharmaceutical composition comprising:
a peptide consisting of SEQ ID NO: 2, SEQ ID NO: 5, SEQ ID NO: 6, SEQ ID NO: 7, or SEQ ID NO: 8, or a pharmaceutically acceptable salt of said peptide; and
a pharmaceutically acceptable carrier or excipient.

9. The pharmaceutical composition according to claim 8, further comprising a cytokine, an immunoenhancement promoting molecule or an antitumor substance.

10. A method for treating an angiogenesis disease or preventing a postoperative tumor recurrence or metastasis, the method including administering to a patient in need thereof, in a therapeutically effective amount, a peptide consisting of SEQ ID NO: 1, SEQ ID NO: 2, SEQ ID NO: 5, SEQ ID NO:

6, SEQ ID NO: 7, or SEQ ID NO: 8, or a pharmaceutically acceptable salt of said peptide.

11. The method of claim 10, wherein the angiogenesis disease comprises liver cancer, lung cancer, esophageal carcinoma, gastric carcinoma, colorectal cancer, renal carcinoma, pancreatic carcinoma, osteosarcoma, or breast carcinoma.

12. The method of claim 10, wherein the peptide or pharmaceutically acceptable salt of the peptide reduces angiogenesis in said patient.

13. The method according to claim 10, wherein the peptide consists of SEQ ID NO: 2, SEQ ID NO: 5, SEQ ID NO: 6, SEQ ID NO: 7, or SEQ ID NO: 8.

14. The method according to claim 10, wherein the angiogenesis disease comprises a hematological malignant tumor.

15. The method according to claim 10, wherein the angiogenesis disease is acute lymphoblastic leukemia, chronic lymphocytic leukemia, acute marrow granulocytic leukemia, chronic marrow granulocytic leukemia, acute malignant myelosclerosis, multiple myeloma, polycythemia vera, waldenstrom macroglobulinemia, hodgkin's lymphoma, or non-hodgkin's lymphoma.

* * * * *